United States Patent
Stransky et al.

(10) Patent No.: US 6,441,237 B1
(45) Date of Patent: Aug. 27, 2002

(54) SUBSTITUTED 3-PHENOXY- AND 3-PHENYLALKYLOXY-2-PHENYL-PROPYLAMINES

(75) Inventors: Werner Stransky, Gau-Algesheim; Matthias Grauert, Ingelheim am Rhein; Adrian Carter, Bingen; Thomas Weiser, Nieder-Olm; Wolf-Dietrich Bechtel, Appenheim; Helmut Ensinger, Ingelheim am Rhein; Ralf Richard H. Lotz, Schemmerhofen; Rainer Palluk, Bingen; Uwe Pschorn, Mainz, all of (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/507,992

(22) Filed: Feb. 18, 2000

Related U.S. Application Data
(60) Provisional application No. 60/130,375, filed on Apr. 21, 1999.

(30) Foreign Application Priority Data

Feb. 20, 1999 (DE) .......................................... 199 07 385

(51) Int. Cl.[7] ........................ C07C 215/00; A61K 31/40
(52) U.S. Cl. ........................ 564/362; 564/347; 564/346; 564/366; 514/317; 514/277; 514/651; 514/427; 514/428; 514/408; 514/471; 546/192; 548/570; 549/490

(58) Field of Search .................................. 564/362, 347, 564/346, 366; 514/317, 651, 277, 427, 428, 408, 471; 546/192; 548/570; 549/490

(56) References Cited

FOREIGN PATENT DOCUMENTS

GB   1343527   *  7/1971

* cited by examiner

*Primary Examiner*—Samuel Barts
(74) *Attorney, Agent, or Firm*—Robert P. Raymond; Timothy X. Witkowski; Mary-Ellen Devlin

(57) ABSTRACT

The present patent application relates to new substituted 3-phenoxy- or 3-phenylalkyloxy-2-phenyl-propylamines of general formula 1, processes for preparing them and their use as pharmaceutical compositions.

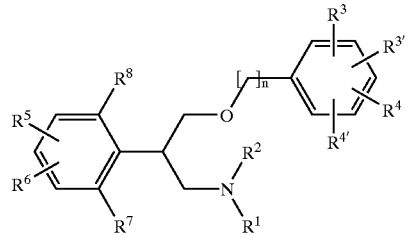

10 Claims, No Drawings

SUBSTITUTED 3-PHENOXY- AND 3-PHENYLALKYLOXY-2-PHENYL-PROPYLAMINES

The application claims benefit of No. 60/130,375 filed Apr. 21, 1999.

The present patent application relates to new substituted 3-phenoxy- or 3-phenylalkyloxy-2-phenyl-propylamines of general formula 1, processes for preparing them and their use as pharmaceutical compositions.

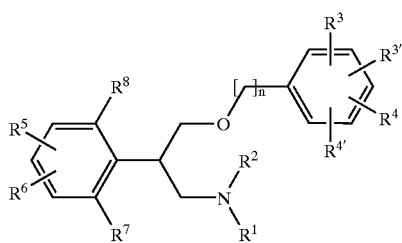

wherein $R_1$ and $R_2$ independently of one another may denote hydrogen, $C_1$–$C_8$-alkyl, benzyl, furylmethyl, cycloalkyl, cycloalkyl-methyl, $C_2$–$C_8$-alkenyl, $C_2$–$C_8$-alkynyl, $C_1$–$C_8$-alkoxy-$(CH_2)_l$—, $C_{3-C8}$-cycloalkoxy-$(CH_2)_m$— and l may denote an integer 1, 2, 3, 4, 5, 6, 7 or 8 and m may denote an integer 0, 1, 2, 3, 4, 5, 6, 7 or 8 or $R_1$ and $R_2$ together with the nitrogen atom form a 3-, 4-, 5-, 6-, 7- or 8-membered heterocyclic ring which may optionally be substituted with 1–4 methyl groups or a dimethylene group; or $R_1$ and $R_2$ together may denote a —$CH_2$—(CH=CH)—$(CH_2)_2$-bridge;

n may denote an integer 0, 1, 2 or 3;

$R_3$, $R_{3'}$, $R_4$ and $R_{4'}$ independently of one another may denote hydrogen, fluorine, chlorine, bromine, hydroxy, methyl, ethyl, methoxy or $CF_3$;

$R_5$ and $R_6$ independently of one another may denote hydrogen, fluorine, chlorine, bromine, methyl, ethyl or $CF_3$ or $R_5$ and $R_6$ adjacent to each other may denote a fused-on aromatic ring;

$R_7$ may denote hydrogen, fluorine, chlorine, methyl, ethyl, methoxy or an aromatic ring fused on at the free vicinal position;

$R_8$ may denote hydrogen, fluorine, chlorine, methyl, ethyl or methoxy.

Preferred compounds of general formula 1 are those wherein $R_1$ and $R_2$ independently of one another may denote hydrogen, $C_1$–$C_6$-alkyl, benzyl, furylmethyl, cycloalkyl, cycloalkyl-methyl, $C_{2-6}$-alkenyl, preferably allyl, $C_2$–$C_6$-alkynyl, preferably propargyl, $C_1$–$C_6$-alkoxy-$(CH_2)_l$—, $C_3$–$C_8$-cycloalkoxy-$(CH_2)_m$— and l denotes an integer 1, 2, 3 or 4, and m denotes an integer 0, 1, 2, 3 or 4, or $R_1$ and $R_2$ together with the nitrogen atom form a 5-, 6-, or 7-membered heterocyclic ring, which may optionally be substituted with 1–4 methyl groups or a dimethylene group;

n may denote an integer 0, 1, 2 or 3;

$R_3$, $R_4$ and $R_{3'}$ independently of one another may denote hydrogen, fluorine, chlorine, bromine, hydroxy, methyl, ethyl, methoxy or $CF_3$;

$R_{4'}$ may denote hydrogen;

$R_5$ and $R_6$ independently of one another may denote hydrogen, fluorine, chlorine, bromine, methyl or ethyl or $R_5$ and $R_6$ adjacent to one another denote a fused-on aromatic ring;

$R_7$ and $R_8$ independently of one another may denote hydrogen, methyl, ethyl, methoxy or fluorine.

Particularly preferred are the compounds of general formula 1, wherein:

$R_1$ and $R_2$ independently of one another may denote hydrogen, $C_1$–$C_6$-alkyl, benzyl, furylmethyl, cycloalkyl, cycloalkyl-methyl, $C_2$–$C_6$-alkenyl, preferably allyl, $C_{2-6}$-alkynyl, preferably propargyl, $C_{1-6}$-alkoxy-$(CH_2)_l$—, $C_3$–$C_8$-cycloalkoxy-$(CH_2)_m$—, and l denotes an integer 1, 2, 3 or 4, and m denotes an integer 0, 1, 2, 3 or 4, or $R_1$ and $R_2$ together with the nitrogen atom form a 5-, 6-, or 7-membered heterocyclic ring, which may optionally be substituted with 1–4 methyl groups or a dimethylene group;

n may denote an integer 0, 1, 2 or 3;

$R_3$ and $R_4$ independently of one another may denote hydrogen, fluorine, chlorine, bromine, hydroxy, methyl, ethyl, methoxy or $CF_3$;

$R_{3'}$ and $R_{4'}$ may denote hydrogen;

$R_5$ and $R_6$ independently of one another may denote hydrogen, fluorine, chlorine, bromine, methyl or ethyl;

$R_7$ and $R_8$ independently of one another may denote hydrogen, methyl, ethyl, methoxy or fluorine.

Of particular interest according to the invention are compounds of general formula 1, wherein:

$R^1$ and $R^2$ independently of one another denote hydrogen, $C_{1-4}$-alkyl, benzyl, furylmethyl, cycloalkyl, cycloalkyl-methyl, $C_{2-4}$-alkenyl, preferably allyl, $C_2$–$C_4$-alkynyl, preferably propargyl, $C_1$–$C_4$-alkoxy-$(CH_2)_l$—, $C_3$–$C_6$-cycloalkoxy-$(CH_2)_m$— and l denotes an integer 1, 2 or 3, and m denotes an integer 1, 2 or 3, or $R^1$ and $R^2$ together with the nitrogen atom form a 5- or 6-membered heterocyclic ring which may optionally be substituted with 1, 2 or 3 methyl groups or a dimethylene group;

n may denote an integer 0, 1, 2 or 3;

$R^3$ may denote fluorine, chlorine or methyl, preferably in the ortho position;

$R^4$ may denote hydrogen, fluorine, chlorine or methyl, preferably in the ortho position;

$R^{3'}$ and $R^{4'}$ may denote hydrogen;

$R^5$ and $R^6$ independently of one another may denote hydrogen or methyl;

$R^7$ and $R^8$ independently of one another may denote methyl, ethyl or methoxy.

Most particularly preferred are compounds of general formula 1, wherein $R^1$ and $R^2$ independently of one another denote hydrogen, methyl, ethyl, propyl, butyl, benzyl, furylmethyl, cyclopentyl, cyclohexyl, cyclopropylmethyl, cyclobutylmethyl, cyclopentylmethyl, cyclohexylmethyl, $C_2$–$C_4$-alkenyl, preferably allyl, $C_2$–$C_4$-alkynyl, preferably propargyl, $C_1$–$C_4$-alkoxy-$(CH_2)_l$—, $C_3$–$C_6$-cycloalkoxy-$(CH_2)_m$—, and l denotes an integer 1, 2 or 3 and m denotes an integer 1, 2 or 3, or $R^1$ and $R^2$ together with the nitrogen atom form a 5- or 6-membered heterocyclic ring which may optionally be substituted with 1 or 2 methyl groups or a dimethylene group;

n may denote 1;

$R^3$ may denote ortho-fluorine, ortho-chlorine or ortho-methyl;

$R^4$ may denote hydrogen, ortho-fluorine, ortho-chlorine or ortho-methyl;

$R^{3'}$ and $R^{4'}$ may denote hydrogen;

$R^5$ and $R^6$ may denote hydrogen;

$R^7$ and $R^8$, which may be identical or different, may denote methyl or ethyl, preferably methyl.

The following compounds are mentioned as examples of compounds of particular interest according to the invention:

N-Pentamethylene-3-(2,6-difluorophenyl)methoxy-2-(2,6-dimethylphenyl)-propylamine;

N-Pentamethylene-3-(2-fluorophenyl)methoxy-2-(2,6-dimethylphenyl)-propylamine;

N-Pentamethylene-3-(2,6-dichlorophenyl)methoxy-2-(2,6-dimethylphenyl)-propylamine;

N-Pentamethylene-3-(2,6-dimethylphenyl)methoxy-2-(2,6-dimethylphenyl)-propylamine;

N-Cyclopropylmethyl-3-(2,6-difluorophenyl)methoxy-2-(2,6-dimethylphenyl)-propylamine;

N-Allyl-3-(2,6-difluorophenyl)methoxy-2-(2,6-dimethylphenyl)-propylamine;

N-(3,3-Dimethylallyl)-3-(2,6-difluorophenyl)methoxy-2-(2,6-dimethylphenyl)-propylamine;

N-(2-Methylallyl)-3-(2,6-difluorophenyl)methoxy-2-(2,6-dimethylphenyl)-propylamine;

N-(1-Methylallyl)-3-(2,6-difluorophenyl)methoxy-2-(2,6-dimethylphenyl)-propylamine.

The invention relates to the compounds in question, optionally in the form of the individual optical isomers, mixtures of the individual enantiomers or racemates and in the form of the free bases or the corresponding acid addition salts thereof with pharmacologically acceptable acids—such as for example acid addition salts with hydrohalic acids—e.g. hydrochloric or hydrobromic acid—or organic acids—such as e.g. oxalic, fumaric or diglycolic acid or methanesulphonic acid.

Unless otherwise stated, the general definitions are used as follows:

$C_1$–$C_4$-alkyl or $C_1$–$C_8$-alkyl generally denotes a branched or unbranched hydrocarbon group having 1 to 4 carbon atom(s), which may optionally be substituted with one or more halogen atoms—preferably fluorine—, which may be identical to or different from one another. The following hydrocarbon groups are mentioned by way of example:

methyl, ethyl, propyl, 1-methylethyl(isopropyl), n-butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2,-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Unless otherwise specified, the preferred groups are lower alkyl groups having 1 to 4 carbon atoms, such as methyl, ethyl, n-propyl, iso-propyl, n-butyl, 1-methylpropyl, 2-methylpropyl or 1,1-dimethylethyl. The definitions propyl, butyl, pentyl, etc., always include the isomeric groups in question.

Accordingly, alkylene denotes a branched or unbranched double-bonded hydrocarbon bridge with 1 to 8 carbon atoms which may optionally be substituted by one or more halogen atom(s)—preferably fluorine—which may be identical to or different from each other.

Cycloalkyl generally represents a saturated or unsaturated cyclic hydrocarbon group with 3 to 9 carbon atoms, which may optionally be substituted with one or more halogen atoms—preferably fluorine—which may be identical to or different from each other. Cyclic hydrocarbons with 3 to 6 carbon atoms are preferred. Examples include cyclopropyl, cyclobutyl, cyclopentyl, cyclopentenyl, cyclohexyl, cyclohexenyl, cycloheptyl, cycloheptenyl, cycloheptadienyl, cyclooctyl, cyclooctenyl, cyclooctadienyl and cyclononinyl.

Alkenyl is generally a branched or unbranched hydrocarbon group with 2 to 8 carbon atoms which may contain one or more double bonds and which may optionally be substituted by one or more halogen atoms—preferably fluorine—whilst the halogens may be identical or different. The following alkenyl groups are mentioned by way of example:

vinyl, 2-propenyl (allyl), 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 3-methyl-4-pentenyl, 4-methyl-4-pentenyl, 1,1-dimethyl-2-butenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl.

Of the lower alkenyl groups which have three or four carbon atoms and a double bond, the allyl group is preferred.

Alkynyl generally denotes a branched or unbranched hydrocarbon group with 2 to 8 carbon atoms which may have one or more triple bonds and may optionally be substituted by one or more halogen atoms—preferably fluorine—, whilst the halogens may be identical or different. The following alkynyl groups are mentioned by way of example:

2-propynyl(propargyl), 2-butynyl, 3-butynyl, 1-methyl-2-propynyl, 2-methyl-2-propynyl, 2-pentynyl, 3-pentynyl, 4-pentynyl, 1-methyl-2-butynyl, 2-methyl-2-butynyl, 3-methyl-2-butynyl, 1-methyl-3-butynyl, 2-methyl-3-butynyl, 3-methyl-3-butynyl, 1,1-dimethyl-2-propynyl, 1,2-dimethyl-2-propynyl, 1-ethyl-2-propynyl, 2-hexynyl, 3-hexynyl, 4-hexynyl, 5-hexynyl, 1-methyl-2-pentynyl, 2-methyl-2-pentynyl, 3-methyl-2-pentynyl, 4-methyl-2-pentynyl, 1-methyl-3-pentynyl, 2-methyl-3-pentynyl, 3-methyl-3-pentynyl, 4-methyl-3-pentynyl, 1-methyl-4-pentynyl, 3-methyl-4-pentynyl, 4-methyl-4-pentynyl, 1,1-dimethyl-2-butynyl, 1,1-dimethyl-2-butynyl, 1,1-dimethyl-3-butynyl, 1,2-dimethyl-2-butynyl, 1,2-dimethyl-3-butynyl, 1,3-dimethyl-2-butynyl, 1,3-dimethyl-3-butynyl, 2,2-dimethyl-3-butynyl, 2,3-dimethyl-2-butynyl, 2,3-dimethyl-3-butynyl, 1-ethyl-2-butynyl, 1-ethyl-3-butynyl, 2-ethyl-1-butynyl, 2-ethyl-2-butynyl, 2-ethyl-3-butynyl, 1,1,2-trimethyl-2-propynyl, 1-ethyl-1-methyl-2-propynyl and 1-ethyl-2-methyl-2-propynyl.

Of the lower alkynyl groups which have three or four carbon atoms and a triple bond, the propargyl group is preferred.

Alkoxy generally denotes a straight-chained or branched hydrocarbon group bound via an oxygen atom—a lower alkoxy group with 1 to 4 carbon atom(s) is preferred. The methoxy group is particularly preferred.

A fused-on aromatic ring, unless otherwise defined, denotes a fused-on benzene ring, for the purposes of the invention.

Biological Properties

The compounds claimed are blockers of the voltage-dependent sodium channel. These are compounds which displace batrachotoxin (BTX) with a high affinity ($K_i$ <1000 nM) competitively or non-competitively from the binding site on the sodium channel. Such substances exhibit "use-dependency" while the sodium channels are blocked, i.e. in order to bind the substances at the sodium channel, the sodium channels first have to be activated. Maximum blockage of the sodium channels is only achieved after repeated stimulation of the sodium channels. Consequently, the substances bind preferentially to sodium channels which are activated a number of times. As a result, the substances are in a position to become effective particularly in those parts of the body which are pathologically overstimulated. The compounds of general formula 1 according to the invention can thus be used to treat diseases which are caused by a functional disorder resulting from overstimulation. These include diseases such as arrhythmias, spasms, cardiac and cerebral ischaemias, pain neurodegenerative diseases of various origins. These include, for example: epilepsy, hypoglycaemia, hypoxia, anoxia, brain trauma, brain oedema, cerebral strokes perinatal asphyxia, degeneration of the cerebellum, amyotropic lateral sclerosis, Huntington's disease, Alzheimer's disease, Parkinson's disease, cyclophrenia, hypotonia, cardiac infarction, heart rhythm disorders, angina pectoris, chronic pain, neuropathic pain and local anaesthesia.

The blocking action on the sodium channel may be demonstrated by the test system which tests the BTX binding to the sodium channel [S.W. Postma & W. A. Catterall, Mol. Pharmacol 25, 219–227 (1984)] as well as by patch-clamp experiments which show that the compounds according to the invention block the electrically stimulated sodium channel in a "use-dependent" manner [W. A. Catterall, Trends Pharmacol. Sci., 8, 57–65 (1987)]. By a suitable choice of cell system (e.g. neuronal, cardiac, DRG cells) it is possible to test the effect of the substances on different subtypes of sodium channel.

The sodium channel blocking property of the compounds according to the invention can be demonstrated by the blocking of the veratridine-induced release of glutamate [S. Villanueva, P. Frenz, Y. Dragnic, F. Orrego, Brain Res. 461, 377–380 (1988)]. Veratridine is a toxin which opens the sodium channel permanently. This leads to an increased influx of sodium ions into the cell. By means of the cascade described above, this sodium influx leads to increased release of glutamate in the neuronal tissue. The compounds according to the invention antagonise this release of glutamate.

The anticonvulsant properties of the substances according to the invention were demonstrated by their protective effect against convulsions triggered by a maximum electric shock in mice [M. A. Rogawski & R. J. Porter, Pharmacol. Rev. 42, 223–286 (1990)].

Neuroprotective properties were demonstrated by a protective effect in a rat MCAO model [U. Pschorn & A. J. Carter, J. Stroke, Cerebrovascular Diseases, 6, 93–99 (1996)] and a malonate-induced lesion model [M. F. Beal, Annals of Neurology, 38, 357–366 (1995) and J. B. Schulz, R. T. Matthews, D. R. Henshaw and M. F. Beal, Neuroscience, 71, 1043–1048 (1996)].

Analgesic effects can be investigated in models of diabetic neuropathy and in a ligature model [C. Courteix, M. Bardin, C. Chantelauze, J. Lavarenne, A. Eschalier, Pain 57, 153–160 (1994); C. Courteix, A. Eschalier, J. Lavarenne, Pain 53, 81–88 (1993); G. J. Bennett and Y.-K. Xie, Pain 33, 87–107 (1988)].

It has also been reported that sodium channel blockers can be used to treat cyclophrenia (manic depressive disorder) [J. R. Calabrese, C. Bowden, M. J. Woyshville; in: Psychopharmacology: The Fourth Generation of Progress (Eds.: D. E. Bloom and D. J. Kupfer) 1099–1111. New York: Raven Press Ltd.].

Methods of Preparation

The claimed compounds 1 can be prepared by methods known from the prior art. One possible method of synthesis is shown in Diagram 1. The starting compounds are the substituted benzylcyanides of the type of general formula 2. Benzylcyanide derivatives of this kind—such as e.g. 2,6-dimethylbenzylcyanides of general formula 2 and their preparation are described in the literature [e.g. Bennett et al., J. Med. Chem. 24, 382–389 (1981); Benington et al. J. Org. Chem. 23, 2034–2035 (1958); Carlin et al. J. Org. Chem. 30, 563–566 (1965)], or may be prepared analogously by these methods.

Diagram 1 (the N protecting group SG is shown here as a BOC protecting group, for example):

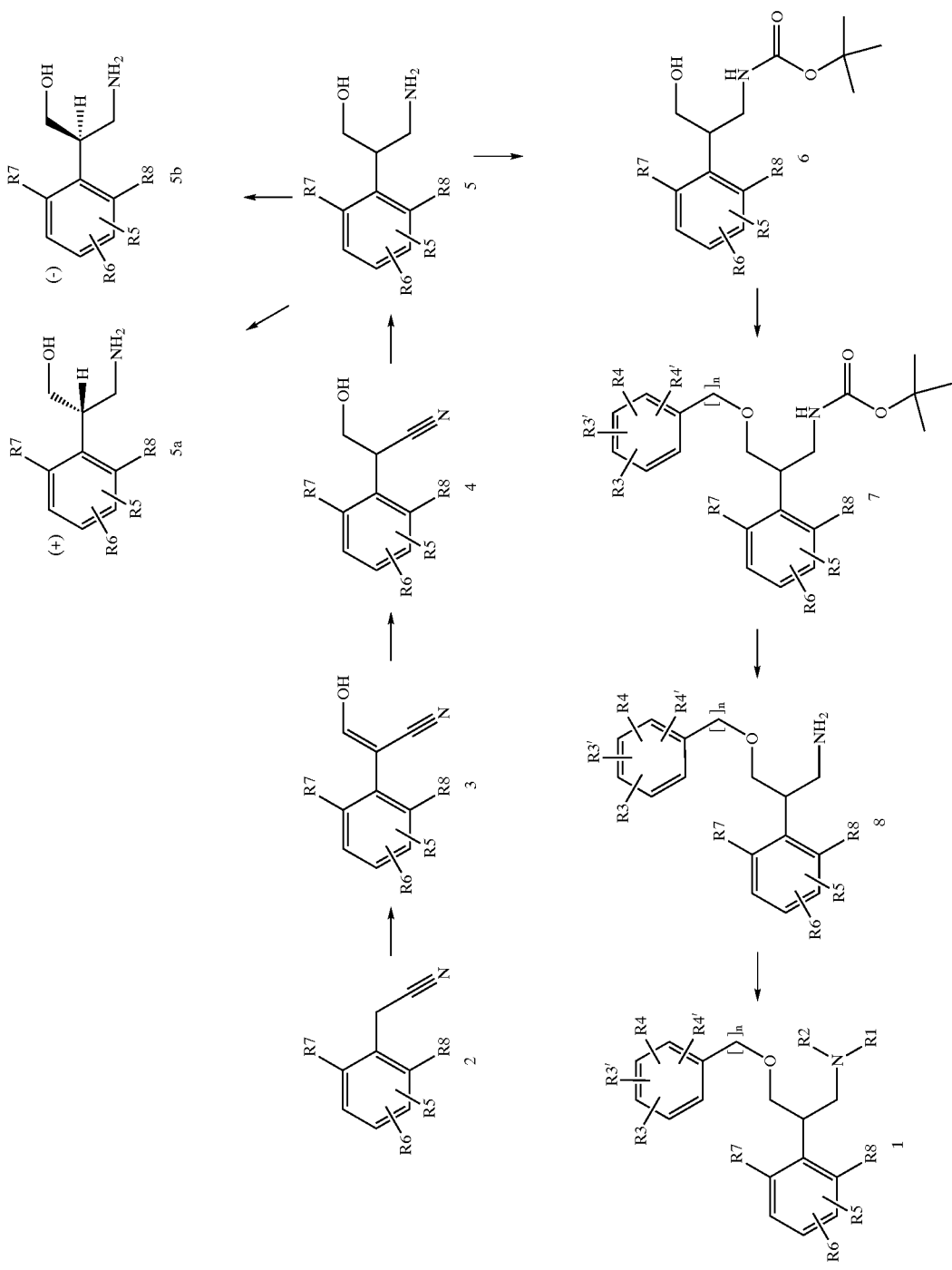

The 2,6-substituted benzylcyanide derivatives of general formula 2 are reacted after deprotonation with formic acid esters, preferably with ethyl formate. The deprotonation may be carried out with any suitable base known from the prior art. Preferably, alkali organyls are used as organometallic bases, particularly alkali metal alkoxides; it is particularly preferable to use potassium tert. butoxide for the deprotonation. The reaction media used may be any aprotic solvents which are inert under the reaction conditions specified and which are suitable for the reaction of deprotonation from the point of view of their physical parameters. Aliphatic or aromatic hydrocarbons in particular are used as solvent, of which—optionally alkyl-substituted—aromatic compounds are preferred; it is particularly preferably to use toluene as reaction medium. The reaction temperature is within a range which is not so low as to make the desired deprotonation difficult or impossible, on the one hand, but it not in a range which makes it possible for side reactions or subsequent reactions to occur. Depending on the particular solvent used a temperature in the range from −20 to +30° C. —preferably in the range from —10 to 20° C. and most preferably in the range from −10 to −5° C. —will be selected, whilst the reaction mixture should appropriately be left to finish reacting at ambient temperature (about 0 to 30° C.). After the hydrolysis has ended the reaction product of type 3 is isolated by extraction, for example, and optionally purified by standard methods known from the prior art, preferably by recrystallisation.

Then the formyl group is reduced to the alcohol of general formula 4 and the nitrile 4 is then reduced to the amine 5. The reduction of the formyl group to the corresponding alcohol well known from the prior art [J. March, Advanced Organic Chemistry, Wiley Interscience, New York (1989), 4th edition, page 910 ff.; C Larock, Comprehensive Organic Transformations, VCH Publishers Inc., New York (1989), p. 527 ff and cit. lit.]. Preferably the reduction is carried out with complex hydrides—such as e.g. with complex alkali boron hydrides or alkali aluminium hydrides or optionally with suitable derivatives thereof, the use of sodium cyanoborohydride being particularly preferred. It is usually advisable to carry out such reductions in the presence of an excess of reduction agent which is preferably one of the abovementioned hydrides, which is in the range from 5 to 100% and preferably in the range from 50 to 100% and most preferably in the range from 70 to 90%. Suitable reaction media are any solvents which do not have a deleterious effect on the course of the reaction. Solvents of this kind are sufficiently well known from the prior art; preferably, branched or unbranched alcohols, particularly lower $C_1$–$C_4$-alkanols, are used, of which methanol is particularly preferred. The reduction may be carried out within a wide temperature range, the choice of temperature being guided particularly by the activity of the complex hydride used, as well as the physical parameters of the reaction medium. The reduction product 4 is isolated, after the destruction of excess reduction agent, in a manner known from the prior art—particularly by extraction.

The reduction of the nitrile 4 thus obtained to the corresponding amine is also known per se from the prior art [J. March, Advanced Organic Chemistry, Wiley Interscience, New York (1985), 3$^{rd}$ edition, pp. 815 ff.; C. Larock, Comprehensive Organic Transformations, VCH Publishers Inc., New York (1989), p. 437 ff. and cit. lit.; P. N. Rylander: Hydrogenation Methods, Academic Press, New York (1985), Chapter 7]. According to the invention, catalytic reduction with hydrogen in the presence of Raney nickel in the presence of an amine—preferably in the presence of ammonia—is preferred. The reaction medium used for the reduction may be any solvent which does not have a detrimental effect on the course of the reaction or, particularly, the activity of the catalyst. Solvents of this kind are known in sufficient numbers from the prior art; preferably, branched or unbranched alcohols—particularly lower $C_1$–$C_4$-alkanols— are used, methanol being particularly preferred. The other parameters of the reaction of reduction may be varied within wide limits and are dependent not only on the educt but particularly on the activity of the Raney nickel which is preferably used. Preferably, the reduction is carried out under a hydrogen pressure in the range from 10 to 200 bar, a hydrogen pressure of 70 bar being particularly preferred. The reaction temperature may be selected within the range from 20 to 150° C.—the reduction is most preferably carried out at 70° C. After the reduction is completed and optionally after the reaction mixture has been cooled, the catalyst is filtered off and the filtrate is purified by methods known from the prior art—wherever possible by distillation (under high vacuum).

At the stage of the aminoalcohol 5 the racemate may optionally be cleaved into the enantiomers. The subsequent cleaving of the resulting mixture of the enantiomeric aminoalcohols of type 5 may be carried out by the methods of enantiomer separation known per se from the prior art—for example by reaction with malic acid, tartaric acid, mandelic acid or camphorsulphonic acid, tartaric acid being particularly preferred.

Thus, for example, reaction with S-(−)-tartaric acid in the case of 3-hydroxy-2-(2,6-dimethylphenyl)-propylamine yields the corresponding enantiomerically pure aminoalcohol of type 5a in the form of its hydrogen tartrate; analogously, the corresponding reaction with R-(+)-tartaric acid yields the enantiomerically pure aminoalcohol of type 5b.

For isomer separation—for example via the corresponding tartrates—the aminoalcohol 5 —for example in the form of the free base—is dissolved in a branched or unbranched $C_1$–$C_4$-alkanol, most preferably in methanol—and combined with the appropriate stereoisomers of one of the abovementioned acids, for example D-(−)-tartaric acid. If necessary a sufficient amount of a nonsolvent with regard to the desired salt—preferably the corresponding hydrogen tartrate—is added, after which the enantiomerically pure isomer of the aminoalcohol 5 crystallises out as the hydrogen tartrate which can be further purified, if necessary, by recrystallisation.

The racemic or enantiomerically pure aminoalcohol 5 or 5a or 5b is reacted in the next step with a compound of type X-S, wherein X denotes a leaving group which can be substituted by an aminonitrogen and S denotes a protecting group suitable for protecting primary amines. Such reagents and methods of binding amine protecting groups thereto are known in large numbers from the prior art [T. W. Greene and P. G. M. Wuts: Protective Groups in Organic Synthesis, John Wiley & Sons, Inc., New York (1991), p. 309 ff.]. According to the invention, in the present instance, the aminonitrogen is preferably selectively N-protected using di-tert.-butyl pyrocarbonate. For this, the racemic or enantiomerically pure aminoalcohol of type 5 or 5a or 5b is dissolved in a solvent which is inert under the reaction conditions specified. Suitable solvents are preferably lower alkyl esters of lower carboxylic acids, of which ethyl acetate is particularly preferred. The reaction with di-tert.-butyl pyrocarbonate is preferably carried out in the temperature range from −20 to 75° C. and most preferably in the range from −10 to +25° C. After the reaction has taken place the solvent is eliminated, the residue is mixed with an aqueous solution of an acidically reacting compound, preferably 90% acetic acid. After about one hour the reaction mixture is evaporated down and the residue is taken up in a suitable solvent, preferably with a lower alkyl ester of a lower carboxylic acid and most preferably with ethyl acetate and after washing with a basically reacting washing solution—preferably with aqueous ammonia solution—the solvent is eliminated.

Then, the alcohol function in the N-protected aminoalcohol of type 6, in the alkaline range, is reacted with correspondingly substituted phenylalkylhalides, resulting in the desired ether structures of general formula 7. The reaction of alcohols of type 6 with phenylalkylhalides—particularly with benzylhalides—is well known from the prior art [C. Larock, Comprehensive Organic Transformations, VCH Publishers Inc., New York, Weinheim (1989), p. 446 ff. and cit. lit.].

In order to prepare the aminoethers of type 7, for example, the protected aminoalcohol of general formula 6 is dissolved in a suitable solvent which is inert under the reaction conditions chosen. Suitable reaction media for carrying out the reaction according to the invention are halogenated lower hydrocarbons, of which halogenated $C_1$- or $C_2$-alkanes are preferred, whilst methylene chloride (dichloromethane) is most preferred as the reaction medium. In the choice of the abovementioned solvent, the use of a phase transfer catalyst has proved particularly advantageous. Phase transfer catalysts of this kind are known in sufficient numbers from the prior art [Römpp, Lexikon Chemie, Georg Thieme Verlag, Stuttgart (1998)]. In the preparation of the compounds according to the invention, so-called tetraalkylammonium compounds have proved particularly suitable. Phase transfer catalysts of this kind according to the invention are quaternary ammonium compounds of type $[R_4N]+$ X— wherein the substituents R, which may be identical or different, are preferably lower alkyl groups. According to the invention, tetrabutylammonium salts are most preferred, of which tetra-n-butylammonium hydrogen sulphate is most preferred.

The aqueous phase used is preferably an aqueous solution of a basically reacting compound of an alkali metal or alkaline earth metal. It is preferable to use an aqueous solution of an alkali metal hydroxide, 50% aqueous sodium hydroxide solution being most preferred.

The reaction with the phenylalkyl derivative, preferably with a phenylalkylhalide and most preferably with a phenylalkylbromide, may be carried out within a wide temperature range the lower limit of which is determined by the reactivity of the reactants and the upper limit of which is determined by the boiling point of the solvent used. Preferably, the reaction of substitution is carried out at a temperature in the range from +5 to 60° C. and most preferably at 0 to 30° C. (which corresponds to ambient temperature for the purposes of the present invention).

After the reaction the organic phase is separated off and the aqueous phase is extracted exhaustively with a suitable solvent—preferably with a halogenated lower hydrocarbon, of which halogenated $C_1$- or $C_2$-alkanes are most preferred, and most preferably with methylene chloride. The combined organic phases are then washed with the aqueous solution of an acidically reacting compound, preferably with the aqueous solution of an inorganic acid and most preferably with 2 N hydrochloric acid, dried and concentrated by evaporation. The residue can then be further purified by methods known per se from the prior art—particularly by crystallisation.

After the protecting group has been cleaved with HCl gas the groups $R_1$ and $R_2$ can then be introduced selectively by alkylation, reductive amination or acylation and subsequent reduction.

For cleaving the protecting group from the aminonitrogen, it should be noted that this is also known from the prior art [T. W. Greene and P. G. M. Wuts: Protective Groups in Organic Synthesis, John Wiley & Sons, Inc., New York (1991), p. 309 ff.]. The subsequent introduction of the groups $R_1$ and $R_2$ at the amino function may take place on the one hand within the scope of an acylation with subsequent reduction. The required carboxylic acid derivatives for this purpose are either known from the prior art or are readily obtained using current methods of synthesis [Houben-Weyl: Methoden der organischen Chemie, volume VIII and volume E5, Georg Thieme Verlag, Stuttgart 1952 or 1985].

For the acylation itself there are a number of methods to choose from [C. Ferri: Reaktionen der organischen Synthese, Georg Thieme Verlag, Stuttgart (1978), p.222 ff. and cit. lit; J. March, Advanced Organic Chemistry, $3^{rd}$ Edition., John Wiley and Sons, New York 1985, p. 370 ff. and cit. lit.; R. C. Larock, Comprehensive Organic Transformation—A Guide to Functional Group Preparations, VCH Verlagsgesellschaft, Weinheim (1989), p. 963 ff. and cit. lit.], whilst reactions with carboxylic acid halides in a solvent which is substantially inert under the prevailing reaction conditions—optionally in the presence of acid-binding agents—such as e.g.: tertiary amines or alkali metal or alkaline earth metal salts—are preferred [A. L. J. Beckwith in J. Zabicki: The Chemistry of Amides, Interscience, New York (1970), p. 73 ff.]. The inert solvents used are generally organic solvents which do not change under the reaction conditions used, such as e.g.: hydrocarbons—for example benzene, toluene, xylene or petroleum fractions—or ethers—such as e.g.: diethylether, glycoldimethylether (glyme), diglycoldimethylether (diglyme)—or cyclic ethers—such as e.g.: tetrahydrofuran (THF), or dioxane—or halogenated hydrocarbons—such as for example dichloromethane (methylene chloride).

Conveniently, the aminoether of general formula 8 is preferably reacted in halogenated hydrocarbons—most preferably in THF—in the presence of acid-binding alkali metal or alkaline earth metal carbonates, most preferably in the presence of potassium carbonate, with the desired acid halides, preferably with the corresponding acid chloride.

However, it is also possible to perform the reaction—in accordance with the so-called Schotten-Baumann variant—in water or in an aqueous alcohol in the presence of alkali metal hydroxides or alkali metal carbonates [Organikum, Organisch-chemisches Grundpraktikum, 19th edition, Johann Ambrosius Barth, Leipzig, Edition Deutscher Verlag der Wissenschaften (1993), p. 424]. Depending on the educts used, it may also prove advantageous to carry out the acylation by the Einhorn variant [Organikum, Organisch-chemisches Grundpraktikum, 19th edition, Johann Ambrosius Barth, Leipzig, Edition Deutscher Verlag der Wissenschaften (1993), p. 424], whilst pyridine is used both as the acid-binding agent and as the reaction medium.

It is also possible to perform the reaction of acylation with the relevant free carboxylic acid [A. L. J. Beckwith in J. Zabicki,: The Chemistry of Amides, Interscience, New York (1970), p. 105 ff.; J. A. Mitchell and E. E. Reid, J. Am. Chem. Soc. 53, (1931) 1879].—It may also prove advantageous to use a mixed anhydride—e.g. with a carbonic acid ester [C. Ferri: Reaktionen der organischen Synthese, Georg Thieme Verlag, Stuttgart (1978), p.222 ff. and cit. lit.; A. L. J. Beckwith in J. Zabicki,: The Chemistry of Amides, Interscience, New York (1970), p. 86 ff.; J. March, Advanced Organic Chemistry, $3^{rd}$ Edition., John Wiley and Sons, New York 1985, p. 371 and cit. lit.; R. C. Larock, Comprehensive Organic Transformations—A Guide to Functional Group Preparations, VCH Verlagsgesellschaft, Weinheim (1989), p. 981 ff. and cit. lit.].

During the preferred acylation with carboxylic acid halides—particularly with carboxylic acid chlorides—the reaction temperature may vary within wide limits, the lower limit being set by too slow a reaction speed and the upper limit being set by the proliferation of undesirable side reactions. In practice, reaction temperatures in the range from −50 to 150° C. and preferably in the range from 0 to 75° C. have proved satisfactory, the reaction temperature chosen naturally being guided by the solvent used. Suitable solvents are, primarily, inert solvents which do not have a detrimental effect on the reaction of acylation. These include mainly ethers—such as e.g.: diethylether, glycoldimethylether (Glyme), diglycoldimethylether (Diglyme)—or cyclic ethers—such as e.g.: tetrahydrofuran (THF), or dioxane, whilst THF is most preferred. The process is usefully carried out with a small excess of the acylating agent in the presence of an acid-binding agent—present in a somewhat greater excess—to ensure the maximum possible reaction of the educts.

In order to obtain the desired aminoether of general formula 1, it is necessary in the last analysis to reduce the resulting acid amide in the subsequent reaction step.—Reductions of acid amides of this kind are also well known from the prior art and may be carried out both by electrolytic reduction, by reduction with alkali metals and by catalytic reduction [R. Schröter in Houben-Weyl: Methoden der organischen Chemie, volume XI/1 and volume E5, Georg Thieme Verlag, Stuttgart 1957, p. 574] or with diborane or hydrogen boride derivatives [J. Furhop and G. Penzlin, Organic Synthesis—Concepts—Methods—Starting Materials—, VCH-Verlagsgesellschaft, Weinheim 1986, p. 90.

However, reduction with complex hydrides, such as alkali boron or alkali aluminium hydrides or with suitable derivatives thereof—optionally in the presence of a catalyst—[N.G. Gaylord: Reduction with Complex Metal hydrides, Wiley, New York (1965); A. Hàjos: Complex hydrides, Elsevier, New York (1979); V. Bazant, M. Capka, M. Cerny, V. Chvalovsky, K. Kochloefl, M. Kraus um M. Màlek, tetrahedron Lett. 9 (1986) 3303] is preferred, the use of lithium aluminium hydride being most preferred.

Suitable reaction media are any inert organic solvents which do not change under the reaction conditions specified. These include ethers—such as for example diethylether, diisopropylether, glycoldimethylether (Glyme), diglycoldimethylether (Diglyme)—or cyclic —ethers—such as e.g.: tetrahydrofuran (THF), or dioxane, of which THF is most preferred, the choice of reaction medium depending inter alia on the nature of the reduction agent used.

When carrying out the reaction it is generally advantageous to perform such reductions in the presence of an excess of the reduction agent, which is preferably one of the abovementioned complex hydrides—particularly lithium tetrahydridoalanate—which is in the range from 5 to 100%—preferably in the range from 10 to 50%. The reactants are normally added while cooling with ice or at ambient temperature and then heated to a reaction temperature in the range from 50 to 150° C., depending on the reactivity of the educts.

Another possible method of preparing the aminoethers of general formula 1 according to the invention from the precursor 8 comprises reacting the amine of type 8 with suitable alkylating agents. These alkylating agents of type $R_1$—Z or $R_2$—Z should conveniently have a suitable leaving group which may be substituted by the amino-nitrogen. Examples of preferred leaving groups of type Z are halogens—such as preferably chlorine, bromine or iodine—or —O—$SO_2$-aryl—such as e.g.: tosylate—or an alkylsulphonate of type —O—$SO_2$-alkyl—such as e.g.: methanesulphonate or halomethanesulphonate or sulphate.—Corresponding alkylating agents are either commercially obtainable or their preparation is known from the prior art.

Suitable solvents are any inert solvents which do not change substantially under the reaction conditions specified and which cannot themselves have a detrimental effect on the course of the reaction as reactive components. These preferably include ethers, such as for example diethylether, diisopropylether, glycoldimethylether (Glyme), diglycoldimethylether (Diglyme), or cyclic ethers, such as e.g.: tetrahydrofuran (THF), or dioxane, or ketones, such as e.g.: methylethylketone or acetone, or acid amides, such as hexamethylphosphotriamide or dimethylformamide (DMF).

It is also possible to use mixtures of the abovementioned solvents. It is particularly preferred to use THF or dimethylformamide (DMF). The reaction of alkylation is preferably carried out in the presence of acid-binding agents, such as e.g.: alkali metal or alkaline earth metal carbonates or hydrogen carbonates.

The reaction temperature may vary within wide limits in the course of the reaction, the lower limit being determined by too slow a reaction speed and the upper limit being determined by the proliferation of side reactions, in practical terms, apart from the corresponding physical values of the solvents. Suitable reaction temperatures are in the range from 0 to 150° C. and, preferably, between 50 and 100° C.

It is also possible to introduce the desired substituents at the amino function by reductive amination [Organikum, Organisch-chemisches Grundpraktikum, $19^{th}$ edition, Johann Ambrosius Barth, Leipzig, Edition Deutscher Verlag der Wissenschaften (1993), p. 451; [C. Ferri: Reaktionen der organischen Synthese, Georg Thieme Verlag, Stuttgart (1978), p.85 ff.]—for example by a Leuckard-Wallach reaction or amination according to Decker/Forster [H. Krauch and W. Kunz, Reaktionen der organischen Chemie, Hüthig Verlag, Heidelberg (1997) p. 104 ff.] and thus arrive at the aminoethers of general formula 1.

During catalytic reductive amination, Raney nickel, optionally doped with other elements—such as e.g. chromium—is generally used. In addition, the reductive amination may also be carried out in the presence of a platinum catalyst, which normally makes it possible to perform the reaction under milder conditions. In general the catalytic reductive amination is performed in the temperature range from 20 to 160° C. The temperature to be adopted depends essentially on the activity of the catalyst, and the reactivity of the amine and carbonyl component. The first choice of solvents will be alcohols or water, lower alcohols—such as methanol, ethanol or isopropanol—being preferred; most preferably, methanol is used as the solvent. The hydrogen pressure may also vary within a wide range and is generally in the range from 1 to 100 atmospheres (1.01 to 101.33 bar), preferably 5 to 80 atmospheres (5.07 to 81.06 bar).

Alternatively, the claimed compounds 1 wherein $R_1$ and $R_2$=—$(CH_2)_m$— (where m preferably denotes 5 or 6) may be prepared by the method illustrated in Diagram 2.

Diagram 2:

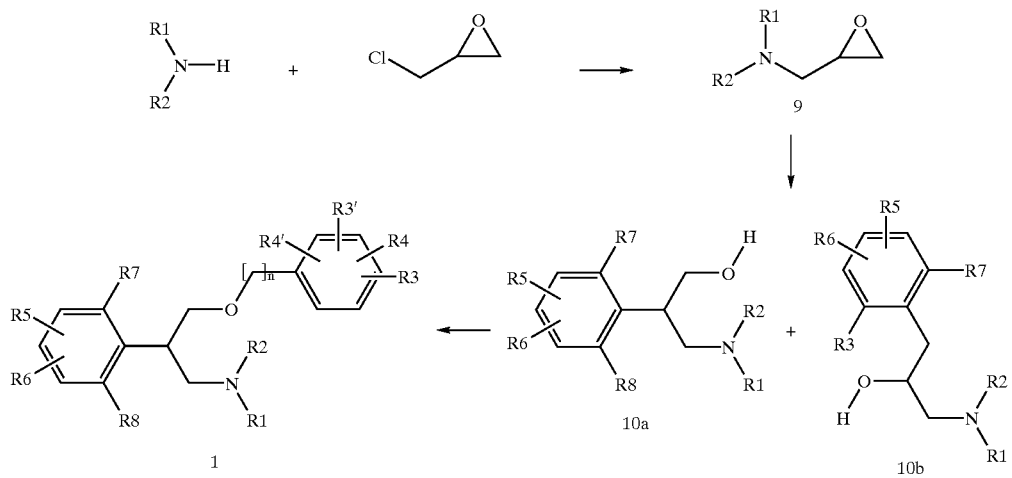

The 3-step reaction sequence may be carried out by the use of racemic epichlorohydrin or R- or S-epichlorohydrin either racemically or stereospecifically - analogously to the methods known from the prior art [J. Amer. Chem. Soc. 80 (1958) 1257]. The amino-oxirane intermediates 9 are appropriately purified by distillation or by flash chromatography, however, they may also be further processed direct s crude products. The intermediate 10a is generated by Grignard reaction and conveniently separated from the unwanted regioisomer 10b by chromatography. The regioisomer ratio can be shifted in favour of 10a if the aminooxirane 9 is combined with one equivalent of $MgCl_2$ etherate and the fine crystalline precipitate formed is reacted with one equivalent of Grignard reagent (inverse addition). Because it is possibly easier to carry out and not only leads to the desired shift of regioisomer but may also result in an increased yield, it may be advantageous to generate a diaryl magnesium reagent (by precipitating $MgBr_2$ with dioxane) and react it with 9 to obtain 10a. The separation of the regioisomers 10 may also be effected after the etherification step in the end compounds of general formula 1. The variation in the chain length(s) is obtained e.g. by using the Mitsunobu reaction, by using benzylhalides or phenylalkylhalides and preferably using potassium tert-butoxide as auxiliary base and by Reppe reaction using optionally substituted phenylacetylene and subsequent hydrogenation of the Z/E-olefin mixtures produced.

The following are examples of pharmaceutical preparations containing the active substance:

Tablets:

| | |
|---|---|
| active substance of general formula 1 | 20 mg |
| magnesium stearate | 1 mg |
| lactose | 190 mg |

Injectable solution

| | |
|---|---|
| active substance of general formula I | 0.3 mg |
| sodium chloride | 0.8 g |
| benzalkonium chloride | 0.01 mg |
| water for injections | ad 100 ml |

A solution similar to that shown above is suitable for nasal administration in a spray, or in conjunction with a device which produces an aerosol with a particle size preferably between 2 and 6 $\mu M$, for administration via the lungs.

Solution for Infusion

A 5% by weight xylitol or saline solution which contains the active substance in a concentration of 2 mg/ml, for example, is adjusted to a pH of about 4 using a sodium acetate buffer.

Infusible solutions of this kind may contain an active substance according to general formula 1 in an amount, based on the total mass of the pharmaceutical preparation, in the range from 0.001 to 5 wt. %, preferably in the range from 0.001 to 3 wt. % and most preferably in the range from 0.01 to 1 wt. %.

Capsules for Inhalation

The active substance according to general formula I in micronised form is packed into hard gelatine capsules (particle size substantially between 2 and 6 $\mu M$), optionally with the addition of micronised carrier substances, such as lactose. It can be inhaled using conventional equipment for powder inhalation. Between 0.2 and 20 mg of active substance and 0 to 40 mg of lactose are packed into each capsule.

Aerosol for Inhalation

| | |
|---|---|
| active substance of general formula I | 1 part |
| soya lecithin | 0.2 parts |
| propellant gas mixture | ad 100 parts |

The Examples which follow serve only to illustrate the invention by way of example without restricting its subject matter.

EXAMPLE 1

Hydroxymethylene-2,6-dimethylphenylacetonitrile (3)

126 g (0.87 mol) of 2,6-dimethylphenylacetonitrile are dissolved in 450 ml toluene and combined with 450 ml of ethyl formate. The mixture is cooled to a temperature of −10° C. and 144 g (1.29 mol) of potassium-tert.-butoxide are added in batches, so that the temperature does not exceed −5° C. It is left to react for a period of 30 minutes (min) at −5° C. and then for 2 hours (h) at ambient temperature. It is then extracted twice with 500 ml of water, the aqueous phase is made acidic with 100 ml of concentrated hydrochloric acid and extracted twice more with 500 ml of methylene chloride (dichloromethane). The organic phase is dried and concentrated by evaporation in vacuo. The residue is recrystallised from petroleum ether. Yield: 139 g (92% of theory).

EXAMPLE 2

3-hydroxy-2-(2,6-dimethylphenyl)-propionitrile (4)

58 g (0.33 mol) of hydroxymethylene-2,6-dimethylphenylacetonitrile are dissolved in 250 ml methanol and combined with 37 g (0.59 mol) of sodium cyanoborohydride. After 2 h, 250 ml of acetic acid are added dropwise, during which time the mixture heats up to 50° C. After the exothermic reaction has died down, the mixture is refluxed for a further 3 h. It is left to cool and the mixture is evaporated down in vacuo. The residue is mixed with 500 g of ice, neutralised with ammonia and extracted twice with 500 ml of ethyl acetate. The combined organic extracts are washed with 100 ml of water. After drying, the solvent is eliminated in vacuo. The residue is further processed from the crude state. 54.1 g (92% of theory) of the title compounds are obtained in the form of an oil.

EXAMPLE 3

3-hydroxy-2-(2,6-dimethylphenyl)-propylamine (5)

52.4 g (0.3 mol) of 3-hydroxy-2-(2,6-dimethylphenyl)-propionitrile are dissolved in 400 ml methanol and combined with 50 9 of $NH_3$. The reaction mixture is hydrogenated under a pressure of 70 bar and at a reaction temperature of 70° C. in the presence of 60 g Raney nickel. After 4 h the mixture is cooled, filtered over silica gel and the solvent is eliminated in vacuo. The residue is distilled under high vacuum. Yield: 40.6 g (76%), boiling point: 135–140° C. (0.02 mbar); melting point of the hydrochloride: 166° C.

EXAMPLE 4.1

(−)-3-hydroxy-2-(2,6-dimethylphenyl)-propylamine-(S)-tartrate (5a)

74.5 g (0.41 mol) of 3-hydroxy-2-(2,6-dimethylphenyl)-propylamine are dissolved in 745 ml methanol and combined with 62.4 g (0.41 mol) of S-(−)-tartaric acid. After 15 min. the crystals precipitated are suction filtered and washed once with 50 ml of methanol and once with 50 ml of diethylether (ether). Then they are recrystallised three times from methanol. Yield: 45.3 g (34%), melting point: 181° C., $[\alpha]_D^{25}$=(−) 21.8° (c=1 in methanol).

The following is prepared analogously to Example 4.1:

EXAMPLE 4.2

(+)-3-hydroxy-2-(2,6-dimethylphenyl)-propylamine-(R)-tartrate: melting point: 181° C., $[\alpha]_D^{25}$=(+) 22.3° (c=1 in methanol).

EXAMPLE 5.1

N-tert.-butoxycarbonyl-3-hydroxy-2-(2,6-dimethylphenyl)-propylamine (6)

14 g (78 mmol) of 3-hydroxy-2-(2,6-dimethylphenyl)-propylamine are dissolved in 140 ml of ethyl acetate and at −10° C. 20.5 g (94 mmol) of di-tert.-butyl pyrocarbonate are added. The mixture is left to react for 1 h at 0° C. and 2 h at RT, the solvent is eliminated in vacuo and 100 ml of 90% acetic acid are added. After 1 h at 50° C. the mixture is concentrated by evaporation in vacuo, the residue is taken up in 200 ml of ethyl acetate and washed twice with 100 ml of 10% ammonia solution. The organic phase is dried and the solvent is eliminated in vacuo. Yield: 19.3 g (89%), oil.

The following are prepared analogously to Example 5.1:

EXAMPLE 5.2

(+)-N-tert.-butoxycarbonyl-3-hydroxy-2-(2,6-dimethylphenyl)-propylamine, melting point: 103° C.

EXAMPLE 5.3

(−)-N-tert.-butoxycarbonyl-3-hydroxy-2-(2,6-dimethylphenyl)-propylamine, melting point: 103° C.

EXAMPLE 6.1

N-tert.-butoxycarbonyl-3-(2,6-difluorophenyl)methoxy-2-(2,6-dimethylphenyl)-propylamine (7)

19 g (68 mmol) of N-tert.-butoxycarbonyl-3-hydroxy-2-(2,6-dimethylphenyl)-propylamine are dissolved in 150 ml $CH_2Cl_2$, mixed with 100 ml of 50% sodium hydroxide solution, 3 g of tetrabutylammonium hydrogen sulphate and 16.5 g (80 mmol) of 2,6-difluorobenzylbromide. The mixture is stirred for 3 h at ambient temperature, the organic phase is separated off and the aqueous phase is extracted once with 100 ml of dichloromethane. The combined organic phases are washed once with 50 ml of 2 N hydrochloric acid, dried and the solvent is eliminated in vacuo. The residue is crystallised from diisopropylether. Yield: 23.5 g (85.1% of theory), melting point: 100° C.

The following are prepared analogously to Example 6.1:

EXAMPLE 6.2

(+)-N-tert.-butoxycarbonyl-3-(2,6-difluorophenyl)methoxy-2-(2,6-dimethylphenyl)-propylamine, melting point: 104° C.

EXAMPLE 6.3

(−)-N-tert.-butoxycarbonyl-3-(2,6-difluorophenyl)methoxy-2-(2,6-dimethylphenyl)-propylamine, melting point: 104° C.

EXAMPLE 6.4

N-tert.-butoxycarbonyl-3-(2-fluorophenyl)methoxy-2-(2,6-dimethylphenyl)-propylamine, oil.

EXAMPLE 6.5

(+)-N-tert.-butoxycarbonyl-3-(2-fluorophenyl)methoxy-2-(2,6-dimethylphenyl)-propylamine, melting point: 102° C.

EXAMPLE 6.6

(−)-N-tert.-butoxycarbonyl-3-(2-fluorophenyl)methoxy-2-(2,6-dimethylphenyl)-propylamine, melting point: 102° C.

EXAMPLE 6.7

N-tert.-butoxycarbonyl-3-(2-chloro-6-fluorophenyl)methoxy-2-(2,6-dimethylphenyl)-propylamine, oil.

EXAMPLE 6.8

N-tert.-butoxycarbonyl-3-(2,6-dimethylphenyl)methoxy-2-(2,6-dimethylphenyl)-propylamine, oil.

EXAMPLE 7.1

3-(2,6-Difluorophenyl)methoxy-2-(2,6-dimethylphenyl)-propylamine-hydrochloride (8)

A strong current of HCl gas is piped into a solution of 23 g (57 mmol) of N-tert.-butoxycarbonyl-3-(2,6-difluorophenyl)methoxy-2-(2,6-dimethylphenyl)-propylamine in 23 ml of ethyl acetate for 3 min. The mixture is left to react for 30 min, the solvent is eliminated in vacuo and the residue taken up in 30 ml of toluene. The solvent is again eliminated in vacuo and the residue crystallised from ether. Yield: 18.5 g (95%), melting point: 123° C.

The following are prepared analogously to Example 7.1:

EXAMPLE 7.2

(+)-3-(2,6-Difluorophenyl)methoxy-2-(2,6-dimethylphenyl)-propylamine-hydrochloride; melting point: 154° C., $[\alpha]_D^{25}$=(+) 9.0° (c=1 in methanol).

EXAMPLE 7.3

(−)-3-(2,6-Difluorophenyl)methoxy-2-(2,6-dimethylphenyl)-propylamine-hydrochloride; melting point: 155° C., $[\alpha]_D^{25}$=(−) 8.9° (c=1 in methanol).

EXAMPLE 7.4

3-(2-Fluorophenyl)methoxy-2-(2,6-dimethylphenyl)-propylamine-tartrate; melting point: 193° C.

EXAMPLE 7.5

(+)-3-(2-Fluorophenyl)methoxy-2-(2,6-dimethylphenyl)-propylamine-hydrochloride; melting point: 145° C., $[\alpha]_D^{25}$=(+) 4.7° (c=1 in methanol).

EXAMPLE 7.6

(−)-3-(2-Fluorophenyl)methoxy-2-(2,6-dimethylphenyl)-propylamine-hydrochloride; melting point: 144° C., $[\alpha]_D^{25}$=(−) 4.5° (c=1 in methanol).

EXAMPLE 7.7

3-(2-chlorine-6-fluorophenyl)methoxy-2-(2,6-dimethylphenyl)-propylamine-hydrochloride; melting point: 128° C.

EXAMPLE 7.8

3-(2,6-dimethylphenyl)methoxy-2-(2,6-dimethylphenyl)-propylamine-hydrochloride; melting point: 154° C.

EXAMPLE 8.1

N-allyl-3-(2,6-difluorophenyl)methoxy-2-(2,6-dimethylphenyl)-propylamine-hydrobromide (1)

1 g (3.3 mmol) of 3-(2,6-difluorophenyl)methoxy-2-(2,6-dimethylphenyl)-propylamine are dissolved in 10 ml of tetrahydrofuran (THF) and stirred with 0.4 g (3.3 mmol) of allylbromide and 1.2 g of $K_2CO_3$ for 16 h at ambient temperature. Then the solvent is eliminated in vacuo, the residue is combined with 50 ml of water and extracted twice with 30 ml of ethyl acetate. The organic phase is dried, concentrated by evaporation in vacuo and the residue is chromatographed on silica gel (methanol/dichloromethane= 2:98). The appropriate fractions are concentrated by evaporation, the residue is dissolved in ether and the hydrobromide is precipitated with HBr/glacial acetic acid. Yield: 1.0 g (71%), melting point: 105° C.

The following are prepared analogously to Example 8.1 (optionally using DMF as solvent):

EXAMPLE 8.2

N-propyl-3-(2,6-difluorophenyl)methoxy-2-(2,6-dimethylphenyl)-propylamine-hydrochloride; melting point: 142° C.

EXAMPLE 8.3

N,N-Dipropyl-3-(2,6-difluorophenyl)methoxy-2-(2,6-dimethylphenyl)-propylamine-hydrobromide; melting point: 143° C.

EXAMPLE 8.4

N-isopropyl-3-(2,6-difluorophenyl)methoxy-2-(2,6-dimethylphenyl)-propylamine-hydrochloride; melting point: 138° C.

EXAMPLE 8.5

N-isobutyl-3-(2,6-difluorophenyl)methoxy-2-(2,6-dimethylphenyl)-propylamine-hydrochloride; melting point: 119° C.

EXAMPLE 8.6

N-cyclopentyl-3-(2,6-difluorophenyl)methoxy-2-(2,6-dimethylphenyl)-propylamine-hydrochloride; melting point: 130° C.

EXAMPLE 8.7

N,N-dimethyl-3-(2,6-difluorophenyl)methoxy-2-(2,6-dimethylphenyl)-propylamine-hydrochloride; melting point: 144° C.

EXAMPLE 8.8

N-cyclopropylmethyl-3-(2,6-difluorophenyl)methoxy-2-(2,6-dimethylphenyl)-propylamine-hydrochloride; melting point: 145° C.

EXAMPLE 8.9

N-propargyl-3-(2,6-difluorophenyl)methoxy-2-(2,6-dimethylphenyl)-propylamine-hydrochloride; melting point: 124° C.

EXAMPLE 8.10

(+)-N-propargyl-3-(2-fluorophenyl)methoxy-2-(2,6-dimethylphenyl)-propylamine-hydrochloride; melting point: 112° C., $[\alpha]_D^{25}$=(+) 6.2° (c=1 in methanol).

EXAMPLE 8.11

(−)-N-propargyl-3-(2-fluorophenyl)methoxy-2-(2,6-dimethylphenyl)-propylamine-hydrochloride; melting point: 112° C., $[\alpha]_D^{25}$=(+)6.30 (c=1 in methanol).

EXAMPLE 8.12

(−)-N-propargyl-3-(2,6-difluorophenyl)methoxy-2-(2,6-dimethylphenyl)-propylamine-hydrochloride; melting point: 145° C., $[\alpha]D^{25}$=(−) 2.2° (c=1 in methanol).

EXAMPLE 8.13

N-methoxyethyl-3-(2,6-difluorophenyl)methoxy-2-(2,6-dimethylphenyl)-propylamine-hydrochloride; melting point: 128° C.

EXAMPLE 8.14

N-propyl-3-(2-fluorophenyl)methoxy-2-(2,6-dimethylphenyl)-propylamine-hydrochloride; melting point: 100° C.

EXAMPLE 8.15

N-isopropyl-3-(2-fluorophenyl)methoxy-2-(2,6-dimethylphenyl)-propylamine-hydrochloride; melting point: 123° C.

EXAMPLE 8.16

N-cyclopentyl-3-(2-fluorophenyl)methoxy-2-(2,6-dimethylphenyl)-propylamine-hydrochloride; melting point: 102° C.

EXAMPLE 8.17

(+)-N-(2-tetrahydrofurylmethyl)-3-(2,6-difluorophenyl)methoxy-2-(2,6-dimethylphenyl)-propylamine-hydrobromide; S-tetrahydrofurfuryl D-camphorsulphonate was used as the electrophile. Melting point: 149° C., $[\alpha]_D^{25}$= (+) 17.8° (c=1 in methanol).

EXAMPLE 8.18

(−)-N-pentamethylene-3-(2,6-difluorophenyl)methoxy-2-(2,6-dimethylphenyl)-propylamine-hydrochloride; 1,5-dibromopentane was used as the electrophile. melting point: 180° C., $[\alpha]_D^{25}$=(−) 7.6° (c=1 in methanol).

EXAMPLE 8.19

N-Pentamethylene-3-(2,6-difluorophenyl)methoxy-2-(2,6-difluorophenyl)-propylamine hydrochloride.

EXAMPLE 9.1

N-(2-R-2-methoxypropyl)-3-(2,6-difluorophenyl)methoxy-2-(2,6-dimethylphenyl)-propylamine-hydrobromide (1)

1.4 g (4.6 mmol) of 3-(2,6-difluorophenyl)methoxy-2-(2,6-dimethylphenyl)-propylamine are dissolved in 20 ml ethyl acetate and combined with 2 g of triethylamine. The mixture is cooled to 0° C. and 2 g (16 mmol) of R-(+)-2-methoxypropionic acid chloride in 10 ml ethyl acetate is added dropwise. After 30 min further reaction the mixture is washed twice with 50 ml of 2 N hydrochloric acid. The organic phase is dried and evaporated down in vacuo. The residue is taken up in THF and 1 g of sodium borohydride (NaBH$_4$) and 3 ml of boron trifluoride etherate (BF$_3$-Et$_2$O) are added. The mixture is left to react for a further 12 hours, 5 ml of water are added and then 30 ml 2 N hydrochloric acid. The THF is eliminated in vacuo. Then 30 ml of ethanol are added and the mixture is heated for 30 min to 70° C. Then the ethanol is eliminated in vacuo, the aqueous phase is combined with 30 ml of ammonia solution and extracted twice with 30 ml of ethyl acetate. The organic phase is dried, concentrated by evaporation in vacuo and the residue is chromatographed on silica gel (methanol/dichloromethane= 2:98). The appropriate fractions are concentrated by evaporation and the residue is dissolved in ether. The hydrobromide is precipitated from the solution with HBr/glacial acetic acid. Yield: 0.9 g (43%), 1:1 mixture of diastereomers, melting point: 154° C.

The following are prepared analogously to Example 9.1:

EXAMPLE 9.2

N-(2-S-2-Methoxypropyl)-3-(2,6-difluorophenyl)methoxy-2-(2,6-dimethylphenyl)-propylamine-hydrobromide; 1:1 mixture of diastereomers, melting point: 151° C.

EXAMPLE 9.3

(−)-N-(2-R-2-Methoxypropyl)-3-(2,6-difluorophenyl)methoxy-2-(2,6-dimethylphenyl)-propylamine-hydrochloride; melting point: 105° C., $[\alpha]_D^{25}$=(−) 15,1° (c=1 in methanol).

EXAMPLE 9.4

(−)-N-(2-R-2-Methoxypropyl)-3-(2,6-difluorophenyl)methoxy-2-(2,6-dimethylphenyl)-propylamine-hydrobromide; melting point: 94° C., $[\alpha]_D^{25}$=(−) 11,1° (c=1 in methanol).

EXAMPLE 9.5

(+)-N-(2-S-2-Methoxypropyl)-3-(2,6-difluorophenyl)methoxy-2-(2,6-dimethylphenyl)-propylamine-hydrobromide; melting point: 131° C., $[\alpha]_D^{25}$=(+) 12,9° (c=1 in methanol).

EXAMPLE 9.6

(+)-N-(2-S-2-Methoxypropyl)-3-(2,6-difluorophenyl)methoxy-2-(2,6-dimethylphenyl)-propylamine-hydrobromide; melting point: 130° C., $[\alpha]_D^{25}$=(+) 10,6° (c=1 in methanol).

EXAMPLE 9.7

(−)-N-(2-R-2-Methoxypropyl)-3-(2-fluorophenyl)methoxy-2-(2,6-dimethylphenyl)-propylamine-diglycolate; melting point: 105° C., $[\alpha]_D^{25}$=(−) 13,3° (c=1 in methanol).

EXAMPLE 9.8

(−)-N-(2-R-2-Methoxypropyl)-3-(2-fluorophenyl)methoxy-2-(2,6-dimethylphenyl)-propylamine-diglycolate; melting point: 77° C., $[\alpha]_D^{25}$=(−) 10,6° (c=1 in methanol)

EXAMPLE 9.9

(+)-N-(2-S-2-Methoxypropyl)-3-(2-fluorophenyl)methoxy-2-(2,6-dimethylphenyl)-propylamine-diglycolate; melting point: 107° C., $[\alpha]_D^{25}$=(+) 13,5° (c=1 in methanol).

EXAMPLE 9.10

(+)-N-(2-S-2-Methoxypropyl)-3-(2-fluorophenyl)methoxy-2-(2,6-dimethylphenyl)-propylamine-diglycolate; melting point: 106° C., $[\alpha]_D^{25}$=(+) 13,4° (c=1 in methanol).

EXAMPLE 9.11

(+)-N-(2-Methoxyethyl)-3-(2,6-difluorophenyl)methoxy-2-(2,6-dimethylphenyl)-propylamine-hydrochloride; melting point: 136° C., $[\alpha]_D^{25}$=(+) 2,5° (c=1 in methanol).

EXAMPLE 9.12

(−)-N-(2-Methoxyethyl)-3-(2,6-difluorophenyl)methoxy-2-(2,6-dimethylphenyl)-propylamine-hydrochloride; melting point: 132° C., $[\alpha]_D^{25}$=(−) 2,5° (c=1 in methanol).

EXAMPLE 9.13

(+)-N-(2-Methoxyethyl)-3-(2-fluorophenyl)methoxy-2-(2,6-dimethylphenyl)-propylamine-hydrochloride; melting point: 77° C., $[\alpha]_D^{25}$=(+) 0,8° (c=1 in methanol).

EXAMPLE 9.14

(−)-N-(2-Methoxyethyl)-3-(2-fluorophenyl)methoxy-2-(2,6-dimethylphenyl)-propylamine-hydrochloride; melting point: 77° C., $[\alpha]_D^{25}$=(−) 1,0° (c=1 in methanol).

EXAMPLE 9.15

N-Methyl-3-(2,6-difluorophenyl)-methoxy-2-(2,6-dimethylphenyl)-propylamine-hydrochloride, ethyl formate was used as the electrophile; melting point: 153° C.

EXAMPLE 9.16

N-Ethyl-3-(2,6-difluorophenyl)-methoxy-2-(2,6-dimethylphenyl)-propylamine-hydrochloride, acetanhydride was used as the electrophile; melting point: 153° C.

EXAMPLE 9.17

(+)-N-Cyclopropylmethyl-3-(2,6-difluorophenyl)-methoxy-2-(2,6-dimethylphenyl)-propylamine-hydrochloride; melting point: 157° C., $[\alpha]_D^{25}$=(+) 4,8° (c=1 in methanol).

EXAMPLE 9.18

(−)-N-Cyclopropylmethyl-3-(2,6-difluorophenyl)-methoxy-2-(2,6-dimethylphenyl)-propylamine-hydrochloride; melting point: 156° C., $[(\alpha]_D^{25}$=(−) 4,8° (c=1 in methanol).

EXAMPLE 9.19

N-Cyclopropylmethyl-3-(2-chloro-6-fluorophenyl)methoxy-2-(2,6-dimethylphenyl)-propylamine-hydrochloride; melting point: 154° C.

EXAMPLE 9.20

N-Cyclopropylmethyl-3-(2,6-dimethylphenyl)methoxy-2-(2,6-dimethylphenyl)-propylamine-hydrochloride; melting point: 142° C.

EXAMPLE 9.21

(+)-N-Cyclopropylmethyl-3-(2-fluorophenyl)methoxy-2-(2,6-dimethylphenyl)-propylamine-hydrobromide; melting point: 101° C., $[\alpha]_D^{25}$=(+) 1,4° (c=1 in methanol).

EXAMPLE 9.22

(−)-N-Cyclopropylmethyl-3-(2-fluorophenyl)methoxy-2-(2,6-dimethylphenyl)-propylamine-hydrochloride; melting point: 101° C., $[\alpha]_D^{25}$=(−) 1,5° (c=1 in methanol).

EXAMPLE 9.23

N-Cyclobutylmethyl-3-(2-fluorophenyl)methoxy-2-(2,6-dimethylphenyl)-propylamine-hydrochloride; melting point: 191° C.

EXAMPLE 9.24

(+)-N-Propyl-3-(2,6-difluorophenyl)-methoxy-2-(2,6-dimethylphenyl)-propylamine-hydrochloride, propionic acid anhydride was used as the electrophile; melting point: 136° C., $[\alpha]_D^{25}$(+) 2,8° (c=1 in methanol).

EXAMPLE 9.25

(−)-N-Propyl-3-(2,6-difluorophenyl)-methoxy-2-(2,6-dimethylphenyl)-propylamine-hydrochloride, propionic acid anhydride was used as the electrophile; melting point: 133° C., $[\alpha]_D^{25}$=(−) 2,3° (c=1 in methanol).

EXAMPLE 9.26

(+)-N-Propyl-3-(2-fluorophenyl)methoxy-2-(2,6-dimethylphenyl)-propylamine-diglycolate, propionic acid anhydride was used as the electrophile; melting point: 115° C., $[\alpha]_D^{25}$=(+) 2,8° (c=1 in methanol).

EXAMPLE 9.27

(−)-N-Propyl-3-(2-fluorophenyl)methoxy-2-(2,6-dimethylphenyl)-propylamine-diglycolate, propionic acid anhydride was used as the electrophile; melting point: 115° C., $[\alpha]_D^{25}$=(−) 2,8° (c=1 in methanol).

EXAMPLE 9.28

(+)-N-Pentyl-3-(2,6-difluorophenyl)-methoxy-2-(2,6-dimethylphenyl)-propylamine-hydrochloride, melting point: 109° C., $[\alpha]_D^{25}$=(+) 3,0° (c=1 in methanol).

EXAMPLE 9.29

(−)-N-Pentyl-3-(2,6-difluorophenyl)-methoxy-2-(2,6-dimethylphenyl)-propylamine-hydrochloride; melting point: 100° C., $[\alpha]_D^{25}$=(−) 3,5° (c=1 in methanol).

EXAMPLE 9.30

(+)-N-Pentyl-3-(2-fluorophenyl)methoxy-2-(2,6-dimethylphenyl)-propylamine-diglycolate; melting point: 106° C., $[\alpha]_D^{25}$=(+) 1.5° (c=1 in methanol).

EXAMPLE 9.31

(−)-N-Pentyl-3-(2-fluorophenyl)methoxy-2-(2,6-dimethylphenyl)-propylamine-diglycolate; melting point: 115° C., $[\alpha]_D^{25}$=(−) 2,0° (c=1 in methanol).

EXAMPLE 10.1

N-benzyl-3-(2,6-difluorophenyl)-methoxy-2-(2,6-dimethylphenyl)-propylamine-hydrochloride (1)

0.6 g (2.0 mmol) of 3-(2,6-difluorophenyl)-methoxy-2-(2,6-dimethylphenyl)-propylamine are stirred with 0.3 g (2.8 mmol) of benzaldehyde for 1 h at 60° C. Then 10 ml of ethanol and 0.3 9 of $NaBH_4$ are added and the mixture is stirred for 30 minutes at 50° C. It is left to cool, 10 ml of 2 N hydrochloric acid are added dropwise and the ethanol is eliminated in vacuo. The residue is combined with 10 ml of conc. ammonia and extracted twice with 30 ml of ethyl acetate. The organic phase is washed with water, dried and concentrated by evaporation in vacuo. The residue is taken up in ether and the hydrochloride is precipitated with ethereal hydrochloric acid. Yield: 0.7 g (81%), melting point: 179° C.

The following were prepared analogously to Example 10.1:

EXAMPLE 10.2

N-Cyclohexyl-3-(2,6-difluorophenyl)-methoxy-2-(2,6-dimethylphenyl)-propylamine-hydrochloride; melting point: 141° C.

EXAMPLE 10.3

N-(2,2-Dimethylpropyl)-3-(2,6-difluorophenyl)-methoxy-2-(2,6-dimethylphenyl)-propylamine-hydrochloride; melting point: 176° C.

EXAMPLE 10.4

N-(2-Furylmethyl)-3-(2,6-difluorophenyl)-methoxy-2-(2,6-dimethylphenyl)-propylamine-hydrochloride; melting point: 136° C.

EXAMPLE 10.5

N-(4-Tetrahydropyranyl)-3-(2,6-difluorophenyl)-methoxy-2-(2,6-dimethylphenyl)-propylamine-hydrochloride; melting point: 176° C.

EXAMPLE 10.6

(+)-N-Isopropyl-3-(2,6-difluorophenyl)-methoxy-2-(2,6-dimethylphenyl)-propylamine-hydrochloride. During the reaction with acetone the water was azeotropically eliminated with toluene; melting point: 107° C., $[\alpha]_D^{25}$=(+) 8.1° (c=1 in methanol).

EXAMPLE 10.7

(+)-N-Isopropyl-3-(2-fluorophenyl)methoxy-2-(2,6-dimethylphenyl)-propylamine-hydrobromide. During the reaction with acetone the water was azeotropically eliminated with toluene; melting point: 111° C., $[\alpha]_D^{25}$=(+) 3.9° (c=1 in methanol).

EXAMPLE 10.8

(−)-N-Isopropyl-3-(2,6-difluorophenyl)-methoxy-2-(2,6-dimethylphenyl)-propylamine-hydrobromide. During the reaction with acetone the water was azeotropically eliminated with toluene; melting point: 112° C., $[\alpha]_D^2$=(−) 4.5° (c=1 in methanol).

Using the methods described hereinbefore (Examples 8.1, 9.1 or 10.1) the following compounds may also be obtained:

EXAMPLE 11.1

(+)-N-Cyclohexylmethyl-3-(2,6-difluorophenyl)-methoxy-2-(2,6-dimethylphenyl)-propylamine-hydrobromide; melting point: 154° C., $[\alpha]_D^{25}$=(+) 2,2° (c=1 in methanol).

EXAMPLE 11.2

(+) -N-Cyclopentylmethyl-3-(2,6-difluorophenyl)-methoxy-2-(2,6-dimethylphenyl)-propylamine-hydrobromide; melting point: 147° C., $[\alpha]_D^{25}$=(+) 4,3° (c=1 in methanol).

EXAMPLE 11.3

(−)-N-Cyclobutylmethyl-3-(2,6-difluorophenyl)-methoxy-2-(2,6-dimethylphenyl)-propylamine-diglycolate; melting point: 138° C., $[\alpha]_D^{25}$=(−) 4,1° (c=1 in methanol).

EXAMPLE 11.4

(−)-N,N-Diallyl-3-(2,6-difluorophenyl)-methoxy-2-(2,6-dimethylphenyl)-propylamine-hydrobromide; melting point: 183° C., $[\alpha]_D^{25}$=(−) 2,8° (c=1 in methanol).

EXAMPLE 11.5

(−)-N,N-Di-(3,3-dimethylallyl)-3-(2,6-difluorophenyl)-methoxy-2-(2,6-dimethylphenyl)-propylamine-hydrobromide; melting point: 139° C., $[\alpha]_D^{25}$=(−) 5,4° (c=1 in methanol).

EXAMPLE 11.6

(+)-N-(3,3-Dimethylallyl)-3-(2,6-difluorophenyl)-methoxy-2-(2,6-dimethylphenyl)-propylamine-hydrobromide; melting point: 175° C., $[\alpha]_D^{25}$=(+) 5.0° (c=1 in methanol).

EXAMPLE 11.6

(−)-N-Cyclopentylmethyl-3-(2,6-difluorophenyl)-methoxy-2-(2,6-dimethylphenyl)-propylamine-hydrobromide; melting point: 147° C., $[\alpha]_D^{25}$=(−) 4,3° (c=1 in methanol).

EXAMPLE 11.8

(+)-N-Cyclobutylmethyl-3-(2,6-difluorophenyl)-methoxy-2-(2,6-dimethylphenyl)-propylamine-diglycolate; melting point: 138° C., $[\alpha]_D^{25}$(+) 4,0° (c=1 in methanol).

EXAMPLE 11.9

(+)-N-Allyl-3-(2,6-difluorophenyl)-methoxy-2-(2,6-dimethylphenyl)-propylamine-hydrobromide; melting point: 142° C., $[\alpha]_D^{25}$=(+) 4,0° (c=1 in methanol).

EXAMPLE 11.10

(−)-N-Allyl-3-(2,6-difluorophenyl)-methoxy-2-(2,6-dimethylphenyl)-propylamine-hydrobromide; melting point: 142° C., $[\alpha]_D^{25}$=(−) 4,3° (c=1 in methanol).

EXAMPLE 11.11

(+)-N,N-Diallyl-3-(2,6-difluorophenyl)-methoxy-2-(2,6-dimethylphenyl)-propylamine-hydrobromide; melting point: 183° C., $[\alpha]_D^{25}$=(+) 2.8° (c=1 in methanol).

EXAMPLE 11.12

(+)-N,N-Di-(3,3-dimethylallyl)-3-(2,6-difluorophenyl)-methoxy-2-(2,6-dimethylphenyl)-propylamine-hydrobromide; melting point: 139° C., $[\alpha]_D^{25}$=(+) 5,0° (c=1 in methanol).

EXAMPLE 11.13

(−)-N-(3,3-Dimethylallyl)-3-(2,6-difluorophenyl)-methoxy-2-(2,6-dimethylphenyl)-propylamine-hydrobromide; melting point: 175° C., $[\alpha]_D^{25}$(−) 6,7° (c=1 in methanol).

EXAMPLE 11.14

(+)-N-(2-Ethylbutyl)-3-(2,6-difluorophenyl)-methoxy-2-(2,6-dimethylphenyl)-propylamine-hydrochloride; melting point: 144° C., $[\alpha]_D^{25}$=(+) 1,5° (c=1 in methanol).

EXAMPLE 11.15

(−)-N-(5-Norbornen-2-yl-methyl)-3-(2,6-difluorophenyl)-methoxy-2-(2,6-dimethylphenyl)-propylamine-hydrochloride; melting point: 145° C., $[\alpha]_D^{25}$= (−) 0,4° (c=1 in methanol).

EXAMPLE 11.16

(+)-N-Pentyl-3-(2,6-difluorophenyl)-methoxy-2-(2,6-dimethylphenyl)-propylamine-hydrochloride; melting point: 120° C., $[\alpha]_D^{25}$=(+) 2,9° (c=1 in methanol).

EXAMPLE 11.17

(+)-N-(3-Methoxypropyl)-3-(2,6-difluorophenyl)-methoxy-2-(2,6-dimethylphenyl)-propylamine-hydrochloride; melting point: 112° C., $[\alpha]_D^{25}$=(+) 5,0° (c=1 in methanol).

EXAMPLE 11.18

(+)-N-(2-Ethoxyethyl)-3-(2,6-difluorophenyl)-methoxy-2-(2,6-dimethylphenyl)-propylamine-hydrochloride; melting point: 123° C., $[\alpha]_D^{25}$=(+) 3,3° (c=1 in methanol).

EXAMPLE 11.19

(−)-N-Cyclohexylmethyl-3-(2,6-difluorophenyl)-methoxy-2-(2,6-dimethylphenyl)-propylamine-hydrobromide; melting point: 155° C., $[\alpha]_D^{25}$=(−) 4,2° (c=1 in methanol).

EXAMPLE 11.20

(−)-N-(2-Ethylbutyl)-3-(2,6-difluorophenyl)-methoxy-2-(2,6-dimethylphenyl)-propylamine-hydrochloride; melting point: 144° C., $[\alpha]_D^{25}$=(−) 2,5° (c=1 in methanol).

EXAMPLE 11.21

(+)-N-(2-Methylpropyl)-3-(2,6-difluorophenyl)-methoxy-2-(2,6-dimethylphenyl)-propylamine-diglycolate; melting point: 126° C., $[\alpha]_D^{25}$=(+) 1,9° (c=1 in methanol).

EXAMPLE 11.22

(−)-N-(2-Methylpropyl)-3-(2,6-difluorophenyl)-methoxy-2-(2,6-dimethylphenyl)-propylamine-diglycolate; melting point: 126° C., $[\alpha]_D^{25}$=(−) 2,8° (c=1 in methanol).

EXAMPLE 11.23

N-Pentamethylene-3-(2,6-difluorophenyl)-methoxy-2-(2,6-dimethoxyphenyl)-propylamine-hydrochloride.

EXAMPLE 11.24

(−)-N-Isopropyl-3-(2,6-difluorophenyl)-methoxy-2-(2,6-dimethylphenyl)-propylamine-hydrochloride; melting point: 114° C., $[\alpha]_D^{25}$=(−) 9.0° (c=1 in methanol).

EXAMPLE 11.25

(−)-N-Pentyl-3-(2,6-difluorophenyl)-methoxy-2-(2,6-dimethylphenyl)-propylamine-hydrochloride; melting point: 126° C., $[\alpha]_D^{25}$=(−) 4.0° (c=1 in methanol).

EXAMPLE 11.26

(−)-N-(2-Ethoxyethyl)-3-(2,6-difluorophenyl)-methoxy-2-(2,6-dimethylphenyl)-propylamine-hydrochloride; melting point: 123° C., $[\alpha]_D^{25}$=(−) 4.3° (c=1 in methanol).

EXAMPLE 11.27

(−)-N-(3-Methoxypropyl)-3-(2,6-difluorophenyl)-methoxy-2-(2,6-dimethylphenyl)-propylamine-hydrochloride; melting point: 83° C., $[\alpha]_D^{25}$=(−) 6.5° (c=1 in methanol).

EXAMPLE 11.28

(+)-N-Tetramethylene-3-(2,6-difluorophenyl)-methoxy-2-(2,6-dimethylphenyl)-propylamine-hydrochloride; melting point: 144° C., $[\alpha]_D^{25}$=(+) 0,3° (c=1 in methanol).

EXAMPLE 11.29

(+)-N-Methyl-N-cyclopropylmethyl-3-(2,6-difluorophenyl)-methoxy-2-(2,6-dimethylphenyl)-propylamine-oxalate; melting point: 136° C., $[\alpha]_D^{25}$=(+) 3,3° (c=1 in methanol).

EXAMPLE 11.30

(+)-N,N-Dimethyl-3-(2,6-difluorophenyl)-methoxy-2-(2,6-dimethylphenyl)-propylamine-hydrochloride; melting point: 147° C., $[\alpha]_D^{25}$=(+) 8,3° (c=1 in methanol).

EXAMPLE 11.31

(+)-N,N-Di-(cyclopropylmethyl)-3-(2,6-difluorophenyl)-methoxy-2-(2,6-dimethylphenyl)-propylamine-hydrobromide; melting point: 181° C., $[\alpha]D^{25}$=(+) 5,5° (c=1 in methanol).

EXAMPLE 11.32

(−)-N-Methyl-N-cyclopropylmethyl-3-(2,6-difluorophenyl)-methoxy-2-(2,6-dimethylphenyl)-propylamine-oxalate; melting point: 136° C., $[\alpha]_D^{25}$=(−) 4,4° (c=1 in methanol).

EXAMPLE 11.33

(−)-N,N-Di-(cyclopropylmethyl)-3-(2,6-difluorophenyl)-methoxy-2-(2,6-dimethylphenyl)-propylamine-hydrobromide; melting point: 181° C., $[\alpha]_D^{25}$=(−) 9,9° (c=1 in methanol).

EXAMPLE 11.34

(−)-N-(4-Fluorobutyl)-3-(2,6-difluorophenyl)-methoxy-2-(2,6-dimethylphenyl)-propylamine-hydrochloride; melting point: 106° C., $[\alpha]_D^{25}$=(−) 3,3° (c=1 in methanol).

EXAMPLE 11.35

(−)-N-(1-Ethylpropyl)-3-(2,6-difluorophenyl)-methoxy-2-(2,6-dimethylphenyl)-propylamine-oxalate; melting point: 127° C., $[\alpha]_D^{25}$=(−) 10,8° (c=1 in methanol).

EXAMPLE 11.36

(−)-N-Cyclobutyl-3-(2,6-difluorophenyl)-methoxy-2-(2,6-dimethylphenyl)-propylamine-hydrochloride; melting point: 107° C., $[\alpha]_D^{25}$=(−) 8,7° (c=1 in methanol).

EXAMPLE 11.37

(−)-N-Methyl-N-isopropyl-3-(2,6-difluorophenyl)-methoxy-2-(2,6-dimethylphenyl)-propylamine-oxalate; melting point: 131° C., $[\alpha]_D^{25}$=(−) 2,5° (c=1 in methanol).

EXAMPLE 11.38

(+)-N-Methyl-N-isopropyl-3-(2,6-difluorophenyl)-methoxy-2-(2,6-dimethylphenyl)-propylamine-oxalate; melting point: 131° C., $[\alpha]_D^{25}$=(+) 1,4° (c=1 in methanol).

EXAMPLE 11.39

(−)-N-(2-Methylallyl)-3-(2,6-difluorophenyl)-methoxy-2-(2,6-dimethylphenyl)-propylamine-hydrobromide; melting point: 155° C., $[\alpha]_D^{25}$=(−) 1,9° (c=1 in methanol).

EXAMPLE 11.40

(+)-N-(2-Methylallyl)-3-(2,6-difluorophenyl)-methoxy-2-(2,6-dimethylphenyl)-propylamine-hydrobromide; melting point: 1550° C., $[\alpha]_D^{25}$(+) 1,3° (c=1 in methanol)

EXAMPLE 11.41

(+)-N-Cyclobutyl-3-(2,6-difluorophenyl)-methoxy-2-(2,6-dimethylphenyl)-propylamine-hydrochloride; melting point: 146° C., $[\alpha]_D^{25}$(+) 8,1° (c=1 in methanol).

EXAMPLE 11.42

(+)-N-(1-Ethylpropyl)-3-(2,6-difluorophenyl)-methoxy-2-(2,6-dimethylphenyl)-propylamine-oxalate; melting point: 131° C., $[\alpha]_D^{25}$(+) 11,6° (c=1 in methanol).

EXAMPLE 11.43

(−)-N-(2-Methylallyl)-N-methyl-3-(2,6-difluorophenyl)-methoxy-2-(2,6-dimethylphenyl)-propylamine-oxalate; melting point: 128° C., $[\alpha]_D^{25}$=(−) 6,7° (c=1 in methanol).

EXAMPLE 11.44

(+)-N-(2-Methylallyl)-N-methyl-3-(2,6-difluorophenyl)-methoxy-2-(2,6-dimethylphenyl)-propylamine-oxalate; melting point: 128° C., $[\alpha]_D^{25}$=(+) 5,5° (c=1 in methanol).

EXAMPLE 11.45

(+)-N-(1-Methylallyl)-3-(2,6-difluorophenyl)-methoxy-2-(2,6-dimethylphenyl)-propylamine-hydrochloride; melting point: 153° C., $[\alpha]_D^{25}$=(+) 4,4° (c=1 in methanol).

EXAMPLE 11.46

(+)-N-(4,5-Dihydro-2-imidazolyl)-3-(2,6-difluorophenyl)-methoxy-2-(2,6-dimethylphenyl)-propylamine-hydrochloride; melting point: 176° C., $[\alpha]_D^{25}$ (+) 25,8° (c=1 in methanol).

EXAMPLE 11.47

(−)-N-(But-2-enyl)-3-(2,6-difluorophenyl)-methoxy-2-(2,6-dimethylphenyl)-propylamine-hydrochloride; melting point: 119° C., $[\alpha]_D^{25}$=(−) 5,4° (c=1 in methanol).

EXAMPLE 11.48

(+)-N-Allyl-N-methyl-3-(2,6-difluorophenyl)-methoxy-2-(2,6-dimethylphenyl)-propylamine-hydrochloride; melting point: 117° C., $[\alpha]_D^{25}$=(+) 3,0° (c=1 in methanol).

EXAMPLE 11.49

(−)-N-(2-Methylallyl)-3-(2,6-difluorophenyl)-methoxy-2-(2,6-dimethylphenyl)-propylamine-hydrochloride; melting point: 172° C., $[\alpha]_D^{25}$=(−) 1,6° (c=1 in methanol).

EXAMPLE 11.50

(+)-N-(2-Methylallyl)-3-(2,6-difluorophenyl)-methoxy-2-(2,6-dimethylphenyl)-propylamine-hydrochloride; melting point: 172° C., $[\alpha]_D^{2}$=(+) 1,5° (c=1 in methanol).

EXAMPLE 11.51

(+)-N-(But-2-enyl)-3-(2,6-difluorophenyl)-methoxy-2-(2,6-dimethylphenyl)-propylamine-hydrochloride; melting point: 121° C., $[\alpha]_D^{25}$=(+) 4,6° (c=1 in methanol).

EXAMPLE 11.52

N-Cyclopropylmethyl-3-(2,6-difluorophenyl)-methoxy-2-(2,4,6-trimethylphenyl)-propylamine-oxalate; melting point: 217° C.;

EXAMPLE 11.53

N-(1-Methyl-1-cyclopropyl-methyl)-3-(2,6-difluorophenyl)-methoxy-2-(2,6-dimethylphenyl)-propylamine-hydrochloride; melting point: 130° C.

EXAMPLE 11.54

N-Butyl-3-(2,6-difluorophenyl)-methoxy-2-(2,4,6-trimethylphenyl)-propylamine-hydrochloride; melting point: 112° C.

EXAMPLE 11.55

(−)-N-Allyl-N-methyl-3-(2,6-difluorophenyl)-methoxy-2-(2,6-dimethylphenyl)-propylamine-hydrochloride; melting point: 116° C., $[\alpha]_D^{25}$=(−) 3,9° (c=1 in methanol).

EXAMPLE 12.1

(S)-4,4-Dimethyl-1-(oxiranylmethyl)-piperidine (9)

The compound is prepared analogously to J. Amer. Chem. Soc. 80; 1958, 1257 by reacting (S)-epichlorohydrin with 4,4-dimethylpiperidine, while the reaction temperature should not exceed 35° C.: Boiling point: 101–104° C./15 mbar.

The following are obtained analogously to Example 12.1:

EXAMPLE 12.2

(S)-3,3-Dimethyl-1-(oxiranylmethyl)-piperidine,

EXAMPLE 12.3

(S)-cis-2,6-Dimethyl-1-(oxiranylmethyl)-piperidine (reaction temperature 60° C.),

EXAMPLE 12.4

(S)-2,2,6,6-Tetramethyl-1-(oxiranylmethyl)-piperidine (reaction temperature 80° C.),

EXAMPLE 12.5

(S)-cis/trans-3,5-Dimethyl-1-(oxiranylmethyl)-piperidine,

EXAMPLE 12.6

(S)-1-(Oxiranylmethyl)-tropane.

EXAMPLE 13.1

(+)-N-Pentamethylene-3-hydroxy-2-(2,6-dimethylphenyl)-propylamine (10a)

From 2.64 g (0.11 mol) of magnesium and 19.4 g (0.105 mol) of 2-bromo-m-xylene in 100 ml of abs. ether, a Grignard solution is prepared which is refluxed for a further hour to complete the reaction. At 25° C. a solution of 14.1 g (0.1 mol) of the (−)-1-(oxiranylmethyl)-piperidine known from the literature, in 100 ml of absolute ether, is then added within 45 minutes, without cooling, and the reaction mixture is refluxed for 1 hour. The mixture is then carefully decomposed at ambient temperature with 100 ml of saturated ammonium chloride solution, the ether phase is separated off, the aqueous phase is extracted once with about 100 ml of ether and, after washing and drying, the combined ether extracts are concentrated by evaporation using the rotary evaporator. The crude product of 10a and 10b obtained is separated in 8–10 g batches using a flash column (h=20 cm, diameter 6 cm, filling 250 g of silica gel 0.04–0.063 mm) with about 3.5 l of methylene chloride/methanol=95/5. The desired regioisomer 10a ($R_f$-value about 0.4, regioisomer 10b $R_f$ value about 0.35) is isolated in a 34% yield. $[\alpha]_D^{20}$= 16.2° (c =2, methanol).

The following are prepared analogously to Example 13.1:

EXAMPLE 13.2

(−)-N-Pentamethylene-3-hydroxy-2-(2,6-dimethylphenyl)-propylamine

EXAMPLE 13.3

R,S-1-N-[2-(2.6-Dimethylphenyl)-3-hydroxy-propyl]-tropane

EXAMPLE 13.4

(+)-N-Pentamethylene-3-hydroxy-2-(2-methylphenyl)-propylamine

EXAMPLE 13.5

R,S-N-Pentamethylene-3-hydroxy-2-(4-chlorophenyl)-propylamine

EXAMPLE 13.6

R,S-N-Pentamethylene-3-hydroxy-2-phenyl-propylamine

EXAMPLE 13.7

R,S-N-Pentamethylene-3-hydroxy-2-(1-naphthyl)-propylamine

EXAMPLE 13.8

R,S-N-Pentamethylene-3-hydroxy-2-(2-naphthyl)-propylamine

EXAMPLE 13.9

(+)-N-(1,5-Dimethylpentamethylene)-3-hydroxy-2-(2,6-dimethylphenyl)-propylamine

EXAMPLE 13.10

R,S-N-Hexamethylene-3-hydroxy-2-(4-chlorophenyl)-propylamine

EXAMPLE 13.11

(+)-N-(3,3-Dimethylpentamethylene)-3-hydroxy-2-(2,6-dimethylphenyl)-propylamine

EXAMPLE 13.12

(+)-N-(2,4-Dimethylpentamethylene)-3-hydroxy-2-(2,6-dimethylphenyl)-propylamine

EXAMPLE 13.13

R,S-N-(1,1,5,5-Tetramethylpentamethylene)-3-hydroxy-2-(2,6-dimethylphenyl)-propylamine

EXAMPLE 13.14

(+)-1-N-[2-(2,6-Dimethylphenyl)-3-hydroxy-propyl]-tropane

EXAMPLE 13.15

R,S-N-Pentamethylene-3-hydroxy-2-(2,3-dimethylphenyl)-propylamine

EXAMPLE 13.16

R,S-N-Pentamethylene-3-hydroxy-2-(2,6-diethylphenyl)-propylamine-hydrochloride, melting point 187–189° C.;

EXAMPLE 13.17

R,S-N-Pentamethylene-3-hydroxy-2-(2,6-dimethylphenyl)-propylamine

Alternatively to the method described in Example 13.1 the following procedure may also be used, which is described hereinafter with reference to the synthesis of the compound N-pentamethylene-3-hydroxy-2-(2,6-dimethylphenyl)-propylamine-hydrochloride (Example 13.17). From 1.82 g (0.076 mol) of magnesium und 10 mL (0.076 mol) of 2-bromo-m-xylene in 40 mL of abs. diethylether a Grignard solution is prepared which is refluxed for about 90 minutes to complete the reaction. At boiling temperature, 6.8 mL of dioxan (0.8 Mol) in 7 mL of abs. diethylether are added dropwide within 2 hours, during which time the magnesium bromide-dioxan complex is precipitated in the form of fine crystals. After the suspension has been stirred for 20 hours at ambient temperature a solution of 5.33 g (0.038 mol) of R,S-1-(oxiranylmethyl)-piperidine in 25 mL abs. diethylether is added dropwise at reflux temperature within 30 minutes. Once the reaction has ended the mixture is decomposed with about 75 mL of saturated ammonium chloride solution and worked up extractively with diethylether. The xylene formed during the reaction is distilled off from the residue remaining in a water jet vacuum. The crude product of the regioisomers obtained (7.04 g) is either purified in 2.5 g batches on silica gel with methylene chloride/methanol=95/5 as eluant or alternatively subjected to the flash chromatography described in Example 13.1. 4.25 g of the compound 13.17 are obtained (45% yield). Melting point 197–198° C. (hydrochloride).

EXAMPLE 14.1

(+)-N-Pentamethylene-3-(2,6-difluorophenyl)-methoxy-2-(2,6-dimethylphenyl)-propylamine-hydrochloride (1)

24.7 g (0.1 mol) of (+)-N-pentamethylene-3-hydroxy-2-(2,6-dimethylphenyl)-propylamine are dissolved in 150 ml of THF and mixed with 13.5 g (0.12 mol) of potassium tert. butoxide. After 10 minutes a solution of 22.8 g (0.11 mol) of 2,6-difluorobenzylbromide in 100 ml of THF is added dropwise at 25–35° C., with cooling, within 30 minutes, stirred for 2 hours and then the reaction mixture is evaporated down at 50° C. using the rotary evaporator. The residue is taken up in 250 ml of methylene chloride and 150 ml of water. After separation of the methylene chloride phase the aqueous phase is extracted with 150 ml of methylene chloride. The combined organic extracts are washed and dried and evaporated down at 40° C. using a rotary evaporator. The residue is purified in roughly 10 g batches through a flash column (cf. Example 13.1) with methylene chloride/methanol=95/5. The 38 g of base thus obtained are dissolved in 114 ml of acetone and ethereal hydrochloric acid is added until a pH of 2–3 is obtained. The mixture is stirred for 30 minutes, the precipitated crystals recrystallised from acetone are suction filtered, and 16.9 g of the target compound are obtained in a 41% yield. Melting point: 176–1780° C., $[\alpha]_d^{20}$=7.5° (c =2, methanol).

The following type 1 compounds are obtained analogously to Example 14.1:

EXAMPLE 14.2

(−)-N-Pentamethylene-3-(2,6-difluorophenyl)-methoxy-2-(2,6-dimethylphenyl)-propylamine-hydrochloride, melting point: 176–178° C.

EXAMPLE 14.3

R,S-N-Pentamethylene-3-(2,6-difluorophenyl)-methoxy-2-(2,6-dimethylphenyl)-propylamine-hydrochloride, melting point: 158–160° C.

EXAMPLE 14.4

(+)-N-Pentamethylene-3-(2-fluorophenyl)methoxy-2-(2,6-dimethylphenyl)-propylamine-hydrochloride, melting point: 126–128° C.

EXAMPLE 14.5

(−)-N-Pentamethylene-3-(2-fluorophenyl)methoxy-2-(2,6-dimethylphenyl)-propylamine-hydrochloride, melting point: 128–130° C.

EXAMPLE 14.6

(+)-N-Pentamethylene-3-(4-chlorophenyl)methoxy-2-(2,6-dimethylphenyl)-propylamine-hydrochloride, melting point: 103–105° C.

EXAMPLE 14.7

(−)-N-Pentamethylene-3-(4-chlorophenyl)methoxy-2-(2,6-dimethylphenyl)-propylamine-hydrochloride, melting point: 118–120° C.

EXAMPLE 14.8

R,S-N-Pentamethylene-3-(4-chlorophenyl)methoxy-2-(2,6-dimethylphenyl)-propylamine-hydrochloride, melting point: 100–101° C.

EXAMPLE 14.9

(+)-N-Pentamethylene-3-phenylmethoxy-2-(2,6-dimethylphenyl)-propylamine-hydrochloride, melting point: 144–146° C.

EXAMPLE 14.10

(+)-N-Pentamethylene-3-(2,6-dichlorophenyl)methoxy-2-(2,6-dimethylphenyl)-propylamine-hydrochloride, oil

EXAMPLE 14.11

(−)-N-Pentamethylene-3-(2,6-dichlorophenyl)methoxy-2-(2,6-dimethylphenyl)-propylamine-hydrochloride, melting point: 70–73° C.

EXAMPLE 14.12

R,S-N-Pentamethylene-3-(2,6-dichlorophenyl)methoxy-2-(2,6-dimethylphenyl)-propylamine-hydrochloride, melting point: 131–133° C.

EXAMPLE 14.13

(+)-N-Pentamethylene-3-(4-bromophenyl)methoxy-2-(2,6-dimethylphenyl)-propylamine-hydrochloride, melting point: 110–112° C.

EXAMPLE 14.14

(−)-N-Pentamethylene-3-(4-bromophenyl)methoxy-2-(2,6-dimethylphenyl)-propylamine-hydrochloride, melting point: 124–127° C.

EXAMPLE 14.15

R,S-N-Pentamethylene-3-(4-bromophenyl)methoxy-2-(2,6-dimethylphenyl)-propylamine-hydrochloride, melting point: 127–129° C.

EXAMPLE 14.16

(+)-N-Pentamethylene-3-(2,6-dimethylphenyl)methoxy-2-(2,6-dimethylphenyl)-propylamine-hydrochloride, melting point: 164–165° C.

EXAMPLE 14.17

(−)-N-Pentamethylene-3-(2,6-dimethylphenyl)methoxy-2-(2,6-dimethylphenyl)-propylamine-hydrochloride, melting point: 162–164° C.

EXAMPLE 14.18

R,S-N-Pentamethylene-3-(2,6-dimethylphenyl)methoxy-2-(2,6-dimethylphenyl)-propylamine-hydrochloride, melting point: 137–139° C.

EXAMPLE 14.19

(+)-N-(1,5-Dimethylpentamethylene)-3-(2,6-difluorophenyl)-methoxy-2-(2,6-dimethylphenyl)-propylamine-hydrochloride, melting point: 85–88° C.

EXAMPLE 14.20

R,S-N-(1,5-Dimethylpentamethylene)-3-(2,6-difluorophenyl)-methoxy-2-(2,6-dimethylphenyl)-propylamine-hydrochloride, melting point: 146–147° C.

EXAMPLE 14.21

R,S-N-(1,5-Dimethylpentamethylene)-3-(2-fluorophenyl)methoxy-2-(2,6-dimethylphenyl)-propylamine-hydrochloride, oil.

EXAMPLE 14.22

R,S-N-(1,1,5,5-Tetramethylpentamethylene)-3-(2,6-difluorophenyl)-methoxy-2-(2,6-dimethylphenyl)-propylamine-hydrochloride, oil.

EXAMPLE 14.23

R,S-1-N-[2-(2,6-Dimethylphenyl)-3-(2-fluorophenyl)methoxy-propyl]-tropane, oil.

EXAMPLE 14.24

R,S-1-N-[2-(2,6-Dimethylphenyl)-3-(2,6-difluorophenyl)-methoxy-propyl]-tropane, oil

EXAMPLE 14.25

(+)-N-(3,3-Dimethylpentamethylene)-3-(2-fluorophenyl)methoxy-2-(2,6-dimethylphenyl)-propylamine-hydrochloride, melting point: 160–161° C.

EXAMPLE 14.26

(+)-N-(3,3-Dimethylpentamethylene)-3-(2,6-difluorophenyl)-methoxy-2-(2,6-dimethylphenyl)-propylamine-hydrochloride, melting point: 180–182° C.

EXAMPLE 14.27

(+)-N-(2,4-Dimethylpentamethylene)-3-(2,6-difluorophenyl)-methoxy-2-(2,6-dimethylphenyl)-propylamine-hydrochloride, E/Z 1:1, oil.

EXAMPLE 14.28

R,S-N-Pentamethylene-3-(2,6-dichlorophenyl)methoxy-2-(1-naphthyl)-propylamine-oxalate, melting point: 192–194° C.

EXAMPLE 14.29

R,S-N-Pentamethylene-3-(2,6-difluorophenyl)-methoxy-2-(1-naphthyl)-propylamine-oxalate, melting point: 140–142° C.

EXAMPLE 14.30

R,S-N-Pentamethylene-3-(4-chlorophenyl)methoxy-2-(1-naphthyl)-propylamine-hydrochloride, oil.

EXAMPLE 14.31

R,S-N-Pentamethylene-3-(4-bromophenyl)methoxy-2-(1-naphthyl)-propylamine-hydrochloride, oil.

EXAMPLE 14.32

R,S-N-Pentamethylene-3-(2,6-dimethylphenyl)methoxy-2-(1-naphthyl)-propylamine-hydrochloride, melting point: 138–140° C.

EXAMPLE 14.33

R,S-N-Pentamethylene-3-(2,6-dichlorophenyl)methoxy-2-(2-naphthyl)-propylamine-hydrochloride, melting point: 158–160° C.

EXAMPLE 14.34

(+)-N-Pentamethylene-3-phenylmethoxy-2-(2-methylphenyl)-propylamine-hydrochloride, oil.

EXAMPLE 14.35

(+)-N-Pentamethylene-3-(2-fluorophenyl)methoxy-2-(2-methylphenyl)-propylamine-hydrochloride, oil.

EXAMPLE 14.36

(+)-N-Pentamethylene-3-(4-bromophenyl)methoxy-2-(2-methylphenyl)-propylamine-hydrochloride, oil.

EXAMPLE 14.37

(+)-N-Pentamethylene-3-(2,6-dimethylphenyl)methoxy-2-(2-methylphenyl)-propylamine-hydrochloride, oil.

EXAMPLE 14.38

(+)-N-Pentamethylene-3-(4-chlorophenyl)methoxy-2-(2-methylphenyl)-propylamine-hydrochloride, oil.

EXAMPLE 14.39

(+)-N-Pentamethylene-3-(2,6-dichlorophenyl)methoxy-2-(2-methylphenyl)-propylamine-hydrochloride, oil.

EXAMPLE 14.40

(+)-N-Pentamethylene-3-(2,6-difluorophenyl)-methoxy-2-(2-methylphenyl)-propylamine-hydrochloride, oil.

EXAMPLE 14.41

R,S-N-Hexamethylene-3-phenylmethoxy-2-(4-chlorophenyl)-propylamine-fumarate, melting point: 109–111° C.

EXAMPLE 14.42

R,S-N-Hexamethylene-3-(2,6-dichlorophenyl)methoxy-2-(4-chlorophenyl)-propylamine-fumarate, melting point: 119–122 ° C.

EXAMPLE 14.43

R,S-N-Hexamethylene-3-(4-chlorophenyl)methoxy-2-(4-chlorophenyl)-propylamine-fumarate, melting point: 113–117° C.

EXAMPLE 14.44

R,S-N-Hexamethylene-3-(2,6-dimethylphenyl)methoxy-2-(4-chlorophenyl)-propylamine-fumarate, melting point: 137–141° C

EXAMPLE 14.45

R,S-N-Pentamethylene-3-(2,6-dimethylphenyl)methoxy-2-(4-chlorophenyl)-propylamine-hydrochloride, melting point: 189–191° C.

EXAMPLE 14.46

(+)-N-Pentamethylene-3-(2,6-dimethylphenyl)methoxy-2-(4-chlorophenyl)-propylamine-hydrochloride, melting point: 159–160° C.

EXAMPLE 14.47

(−)-N-Pentamethylene-3-(2,6-dimethylphenyl)methoxy-2-(4-chlorophenyl)-propylamine-hydrochloride, melting point: 159–160° C.

EXAMPLE 14.48

R,S-N-Pentamethylene-3-(2,6-dichlorophenyl)methoxy-2-(4-chlorophenyl)-propylamine-hydrochloride, melting point: 155–156° C.

EXAMPLE 14.49

R,S-N-Pentamethylene-3-(2,6-difluorophenyl)-methoxy-2-(4-chlorophenyl)-propylamine-hydrochloride, oil.

EXAMPLE 14.50

R,S-N-Pentamethylene-3-(3-phenylpropyl)oxy-2-(4-chlorophenyl)-propylamine, oil.

EXAMPLE 14.51

R,S-N-Pentamethylene-3-(2,6-difluorophenyl)-methoxy-2-phenyl-propylamine-hydrochloride, melting point: 118–119° C.

EXAMPLE 14.52

R,S-N-Pentamethylene-3-(4-bromophenyl)methoxy-2-phenyl-propylamine-hydrochloride, melting point: 158° C.

EXAMPLE 14.53

R,S-N-Pentamethylene-3-(2,6-difluorophenyl)-methoxy-2-(2,3-dimethylphenyl)-propylamine, melting point: 82,4° C.

EXAMPLE 14.54

R,S-N-Pentamethylene-3-(2-fluorophenyl)methoxy-2-(2,3-dimethylphenyl)-propylamine-hydrochloride, oil

EXAMPLE 14.55

R,S-N-Pentamethylene-3-[3,5-di(trifluoromethyl)phenyl]-methoxy-2-(2,3-dimethylphenyl)-propylamine-hydrochloride, melting point: 190.6° C.

EXAMPLE 14.56

(S)-N-Pentamethylene-3-[3,5-di(trifluoromethyl)phenyl]-methoxy-2-(2,6-dimethylphenyl)-propylamine-hydrochloride, melting point: 158° C.

EXAMPLE 14.57

R,S-N-Pentamethylene-3-(2,6-dimethylphenyl)methoxy-2-(2,3-dimethylphenyl)-propylamine-hydrochloride, melting point: 173.5° C.

EXAMPLE 14.58

R,S-N-Pentamethylene-3-(2,6-dichlorophenyl)methoxy-2-(2,3-dimethylphenyl)-propylamine-hydrochloride, oil.

EXAMPLE 14.59

R,S-N-Pentamethylene-3-(2,6-difluorophenyl)-methoxy-2-(2,6-diethylphenyl)-propylamine, oil.

EXAMPLE 14.60

(S)-N-Pentamethylene-2-(2,6-dimethylphenyl)-3-[3-(2,6-difluorophenyl)propoxy]-propylamine-hydrochloride; melting point: 189–190° C.; sodium hydride is used as acid acceptor.

EXAMPLE 15.1

R,S-N-pentamethylene-3-(2-fluorophenoxy)-2-(2,6-dimethylphenyl)-propylamine-hydrochloride (1)

According to Mitsunobu, 2.5 g (0.01 mol) of R,S-N-pentamethylene-2-(2,6-dimethylphenyl)-3-hydroxypropylamine, 0.9 ml of (0.01 mol) of 2-fluorophenol and 2.6 g (0.01 mol) of triphenylphosphine are placed in 30 ml of absolute THF. At ambient temperature a solution of 1.6 ml (0.01 mol) of diethyl azodicarboxylate in about 5 ml of abs. THF is added dropwise. After stirring overnight the reaction mixture is kept for 3 hours at 60° C., the THF is distilled off, the residue is suspended in ether and made acidic with 2 N hydrochloric acid. After the ether has been separated off, the aqueous phase is made alkaline, extracted with methylene chloride and the residue is purified by flash chromatography (eluant ethyl acetate/cyclohexane=25/75). The 1.4 g of colourless oil obtained are dissolved in a little acetone and converted into the hydrochloride with ethereal hydrochloric acid. 0.9 g of white crystals are obtained, melting point: 194–196° C.

The following compounds are prepared analogously to Example 15.1:

EXAMPLE 15.2

R,S-N-Pentamethylene-3-(2,6-difluorophenoxy)-2-(2,6-dimethylphenyl)-propylamine-hydrochloride, melting point: 152–154° C.

EXAMPLE 15.3

R,S-N-Pentamethylene-3-(4-chlorophenoxy)-2-phenyl-propylamine-fumarate, melting point: 114–115° C.

EXAMPLE 15.4

R,S-N-Pentamethylene-3-phenoxy-2-phenyl-propylamine-hydrochloride, melting point: 152–154° C.

EXAMPLE 15.5

N-Pentamethylene-3-(4-bromophenoxy)-2-phenyl-propylamine-hydrochloride, melting point: 206° C.

EXAMPLE 16.1

R,S-N-pentamethylene-2-(2,6-dimethylphenyl)-3-(2-fluorophenylethoxy)-propylamine-hydrochloride 2.5 g (0.01 mol) of R,S-N-pentamethylene-2-(2,6-dimethylphenyl)-3-hydroxy-propylamine and 0.6 g (0.01 mol) of powdered potassium hydroxide are stirred for 15 minutes in DMSO (dimethylsulphoxide), then mixed with 1.2 g (0.01 mol) of o-fluorophenylacetylene and stirred for a further 4 hours at 70° C. The reaction mixture is mixed with water, extracted with methylene chloride and, after washing and drying, the solvent is eliminated. The oily residue is purified by flash chromatography (eluant: 1 litre of ethyl acetate/cyclohexane=25/75) and the resulting Reppe product (2.6 g of Z/E mixture) is hydrogenated, without further purification, with 0.5 g of Pd/BaSO$_4$ in 30 ml of methanol at 5 bar and at ambient temperature over a period of 3.5 hours. The reaction mixture is filtered, the solvent is eliminated and the residue is purified by flash chromatography (eluant:ethyl acetate/cyclohexane=1/1). The residue of 0.4 g is converted into the hydrochloride with acetone/ethereal hydrochloric acid and crystallised by trituration with ether. 0.3 g of colourless crystals are obtained, melting point: 123–124° C.

What is claimed is:
1. A compound of general formula 1

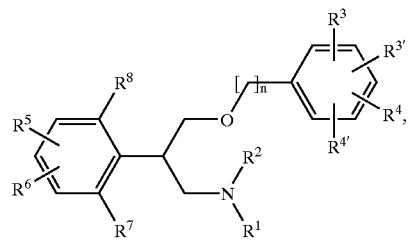

wherein:
R$^1$ and R$^2$ independently of one another are hydogen, C$_1$–C$_4$-alkyl, benzyl, furylmethyl, cycloalkyl, cycloalkyl-methyl, C$_2$–C$_4$-alkenyl, C$_2$–C$_4$-alkynyl, C$_1$–C$_4$-alkoxy-(CH$_2$)$_1$—, or C$_3$–C$_6$-cycloalkoxy-(CH$_2$)$_m$—, wherein 1 is an integer 1, 2, or 3, and m is an integer 1, 2, or 3, or R$^1$ and R$^2$ together with the nitrogen atom form a 5- or 6-membered heterocyclic ring which is optionally substituted with 1, 2, or 3 methyl groups or a dimethylene group;

n is an integer 0, 1, 2, or 3;

R$^3$ is fluorine, chlorine, or methyl;

R$^4$ is hydrogen, fluorine, chlorine, or methyl;

R$^{3'}$ and R$^{4'}$ is hydrogen;

R$^5$ and R$^6$ independently of one another is hydrogen or methyl; and

R$^7$ and R$^8$ independently of one another is methyl, ethyl, or methoxy, or an optical isomer or corresponding acid addition salt with pharmacologically acceptable acids.

2. The compound of general formula 1 according to claim 1, wherein:

R$^1$ and R$^2$ independently of one another are hydrogen, C$_1$–C$_4$-alkyl, C$_2$–C$_4$-alkenyl, or C$_2$–C$_4$-alkynyl;

R$^3$ is methyl;

R$^4$ is hydrogen or methyl; and

R$^7$ and R$^8$ independently of one another is methyl or ethyl, or an optical isomer or corresponding acid addition salt with pharmacologically acceptable acids.

3. The compound of general formula 1 according to claim 1, wherein: R$^1$ and R$^2$ independently of one another are benzyl, furylmethyl, cycloalkyl, cycloalkyl methyl, C$_1$–C$_4$-alkoxy-(CH$_2$)$_1$—, or C$_3$–C$_6$-cycloalkoxy-(CH$_2$)$_m$—, wherein 1 is an integer 1, 2, or 3, and m is an integer 1, 2, or 3, or an optical isomer or corresponding acid addition salt with pharmacologically acceptable acids.

4. The compound of general formula 1 according to claim 1, wherein:

R$^1$ and R$^2$ together with the nitrogen atom form a 5- or 6-membered heterocyclic ring which is optionally substituted with 1, 2, or 3 methyl groups or a dimethylene group, or an optical isomer or corresponding acid addition salt with pharmacologically acceptable acids.

5. The compound of general formula 1 according to claim 1, wherein:

R$^3$ is fluorine or chlorine; and

R$^4$ is fluorine or chlorine, or an optical isomer or corresponding acid addition salt with pharmacologically acceptable acids.

6. A pharmaceutical preparation comprising a compound according to one of claims 1 or 2 to 5 and a conventional excipient or carrier.

7. A pharmaceutical preparation according to claim 6, wherein the pharmaceutical preparation is a solution for infusion.

8. A method for the therapeutic treatment of functional disorders caused by overstimulation in a patient in need thereof, the method comprising administering to the patient an effective amount of a compound according to one of claims 1 or 2 to 5.

9. A method for the therapeutic treatment of arrhythmias, spasms, cardiac and cerebral ischemias, pain and neurodegenerative disorders of various origins in a patient in need thereof, the method comprising administering to the patient an effective amount of a compound according to one of claims 1 or 2 to 5.

10. A method for the therapeutic treatment of epilepsy, hypoglycemia, hypoxia, anoxia, brain trauma, brain edema, cerebral stroke, perinatal asphyxia, degeneration of the cerebellum, amyotrophic lateral sclerosis, Huntington's disease, Alzheimer's disease, Parkinson's disease, cyclophrenia, hypotonia, cardiac infarct, heart rhythm disorders, angina pectoris, chronic pain, neuropathic pain, and local anesthesia in a patient in need thereof, the method comprising administering to the patient an effective amount of a compound according to one of claims 1 or 2 to 5.

* * * * *